(12) United States Patent
Cheng et al.

(10) Patent No.: US 8,680,760 B2
(45) Date of Patent: Mar. 25, 2014

(54) BETA-DIKETONE ANCILLARY LIGANDS AND THEIR METAL COMPLEXES USED IN ORGANIC OPTOELECTRONIC DEVICES

(75) Inventors: Chien-Hong Cheng, Hsinchu (TW); Fang-Iy Wu, Hsinchu (TW); Chin-Hsien Chen, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 367 days.

(21) Appl. No.: 12/766,011

(22) Filed: Apr. 23, 2010

(65) Prior Publication Data

US 2010/0270915 A1     Oct. 28, 2010

(30) Foreign Application Priority Data

Apr. 23, 2009   (TW) ................................ 98113422 A

(51) Int. Cl.
*H01J 1/63*       (2006.01)
*C07F 15/00*    (2006.01)

(52) U.S. Cl.
USPC ............... 313/504; 546/2; 548/101; 548/402; 556/13

(58) Field of Classification Search
USPC .......... 313/504; 546/2; 548/101, 402; 556/13
See application file for complete search history.

(56) References Cited

FOREIGN PATENT DOCUMENTS

JP          2009071107 A   *   4/2009   .............. H01L 51/50

* cited by examiner

*Primary Examiner* — Joseph Kosack
(74) *Attorney, Agent, or Firm* — WPAT, PC; Justin King

(57) ABSTRACT

The present invention discloses a phosphor material for organic optoelectronic devices. The phosphor is a complex comprising a metal (Ir or Pt) and an aryl-modified beta-diketone ligand. The complexes of this invention are useful to function as an emitter in the emissive layer of an organic light emitting diode, even as the complex is the main component of this layer.

18 Claims, 4 Drawing Sheets

BETA-DIKETONE ANCILLARY LIGANDS AND THEIR METAL COMPLEXES USED IN ORGANIC OPTOELECTRONIC DEVICES

BACKGROUND OF THE INVENTION

1. Field of the Invention

The present invention is generally related to a phosphor and the application thereof, and more particularly to a phosphor comprising metal (Ir or pt) complex and the application thereof.

2. Description of the Prior Art

Generally, the fundamental structure of an Organic Light Emitting Diodes (OLEDs) includes a cathode, an anode, and an emissive layer (EML). When electron or hole does not easily reach the emissive layer, a hole-transport layer (HTL) can be positioned between the anode and the emissive layer, and/or an electron transporting layer (ETL) can be positioned between the cathode and the emissive layer.

In a conjugated molecule, an electron at ground state can adsorb energy and transit to an exciting state. An electron at exciting state can be back to ground state through the pathway of internal conversion, intersystem crossing, and external conversion. When an electron is back to ground state from a single exciting state by photo emission, the process is called fluorescence. If an electron back to ground state from a triplet exciting state, the resulting radiative transition is called phosphorescence. Under the influence of an external electric field, singlet (fluorescence) and triplet (phosphorescence) excitons can be formed in a ratio of 1:3 within an OLED device. By incorporating phosphor into an OLED device, both kinds of excitons can be harvested for light emission by strong spin-orbit coupling of the heavy metal. The color of the emitting light is depended on the energy gap between the exciting state and the ground state. Therefore, the wanted emitting color can be modulated by modifying the molecular structure to change the energy gap.

One of the most competitive advantages of OLED lighting relative to other existing lighting technologies is its flat homogeneous illumination characteristic. To obtain white light from an OLED, three primary color, red, green, and blue (RGB), or two complementary color, like blue and orange, dopants are normally doped in a single EML or separate EMLs, and thereby the structure of White OLEDs (WOLEDs) is more complicate than those of monochromatic OLEDs. For doped WOLEDs, the precise control of doping ratio for each dopant emitter throughout entire active area is required for an ideal lighting panel. However, as larger number of EMLs or dopants involved, the manufacturing process will become more difficult and costly. In light of the above-mentioned problems, it is an important target to develop a new emitting material for high performance WOLED with a simple device structure. This remains an important research aspect in the industrial practical applications.

SUMMARY OF THE INVENTION

In view of the above background and to fulfill the industrial requirements, a new phosphorescence material and the application thereof are disclosed in this specification.

This present specification discloses a phosphor material comprises a transition metal $M^1$, and an aryl substituted beta-diketone ancillary ligand, wherein $M^1$ is selected from Pt or Ir. The general formula of the mentioned phosphor material is:

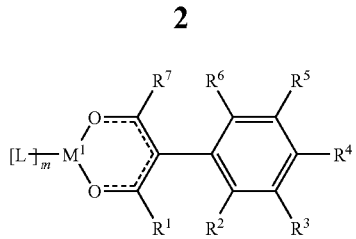

Referred to the formula, L is a ligand, and m is 1 or 2. $R^1$ and $R^7$ can be identical or different, and $R^1$ and $R^7$ are independently selected from the group consisting of the following: H atom, halogen atom (such as fluorine, chlorine, bromine, and iodine), C1-C22 alkyl group, and C1-C22 haloalkyl group. $R^2$, $R^3$, $R^4$, $R^5$, and $R^6$ can be identical or different, and $R^2$, $R^3$, $R^4$, $R^5$, and $R^6$ are independently selected from the group consisting of the following: H atom, halogen atom, C1-C22 alkyl group, and C1-C22 haloalkyl group, C6-C22 aryl group, and 5 to 7 members heterocyclic group with 1 to 4 heteroatom(s) selected from N, O, B, P, Si.

When employing the above-mentioned phosphor material having aryl substituted beta-diketone as the dopant in a phosphorescent EML at high doping levels, the device performance will be better than that obtained from the phosphorescent EML using the corresponding phosphor with respective non-substituted beta-diketone ligand as the dopant.

Besides, when the concentration of the dopant is raised, with increasing the size of the aryl substituted beta-diketone ancillary ligand, the intermolecular interaction will be decreased so that the triplet-triplet annihilation and concentration quenching can be restrained. Moreover, the aryl modification on the beta-diketone ligand of the mentioned formula will not affect the emission spectral position of the complex in diluted solution. If the introduced aryl substituent(s) with electron/hole transporting property, the injection and transport of electron/hole in the EML will be improved. When M1 is Pt, the geometric configuration of the complex is square planar. When the size of the aryl substituent(s) is increased, the π-π (stacking of the molecules will be restrained. So that the property of aggregated state emission will be decreased, and the emission will shift to blue.

BRIEF DESCRIPTION OF THE DRAWINGS

The present disclosure can be described by the embodiments given below. It is understood, however, that the embodiments below are not necessarily limitations to the present disclosure, but are used to a typical implementation of the invention.

DESCRIPTION OF THE PREFERRED EMBODIMENTS

Figure 1A:
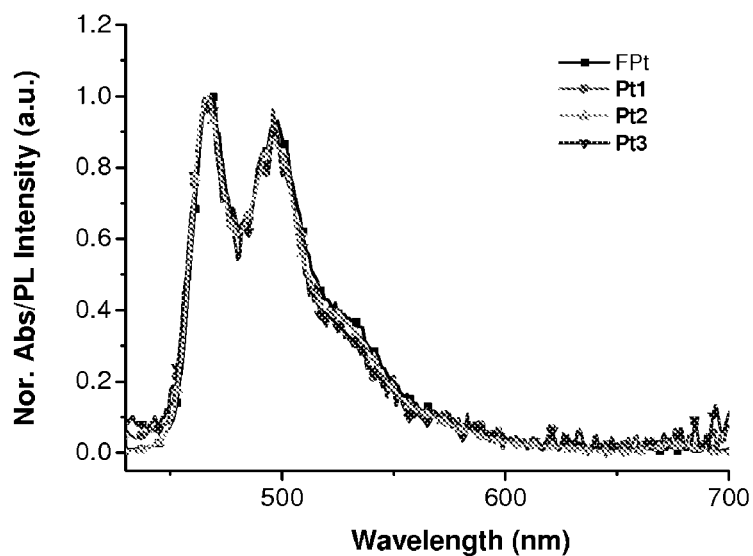
FIG. 1A illustrates the Photoluminescence spectra of FPt and Pt complexes (Pt 1, Pt 2, and Pt 3) in diluted solution at room temperature.

What probed into the invention are a phosphor material and the application thereof. Detailed descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

The first embodiment according to this specification discloses a phosphor material. The mentioned phosphor material comprises a transition metal $M^1$, and an aryl-substituted beta-diketone ancillary ligand. The general formula of the mentioned phosphor material is as the following.

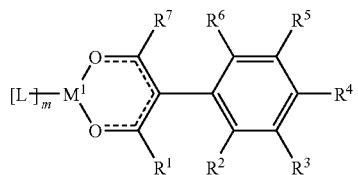

Referred to the formula, L is a ligand, and m is 1 or 2. $R^1$ and $R^7$ can be identical or different, and $R^1$ and $R^7$ can be independently selected from the group consisting of the following: H atom, halogen atom (such as fluorine, chlorine, bromine, and iodine), C1-C22 alkyl group, and C1-C22 halo-alkyl group. $R^2$, $R^3$, $R^4$, $R^5$, and $R^6$ can be identical or different, and $R^2$, $R^3$, $R^4$, $R^5$, and $R^6$ are independently selected from the group consisting of the following: H atom, halogen atom, C1-C22 alkyl group, and C1-C22 halo-alkyl group, C6-C22 aryl group, and 5 to 7 members heterocyclic group with 1 to 4 heteroatom(s) selected from the group consisting of the following: N, O, B, P, and Si. The mentioned heterocyclic group(s) is/are selected from one of the following or the combination thereof:

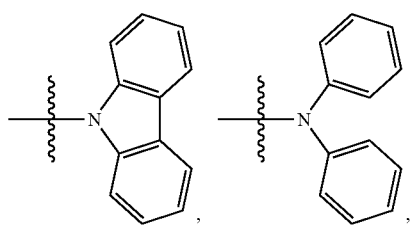

-continued

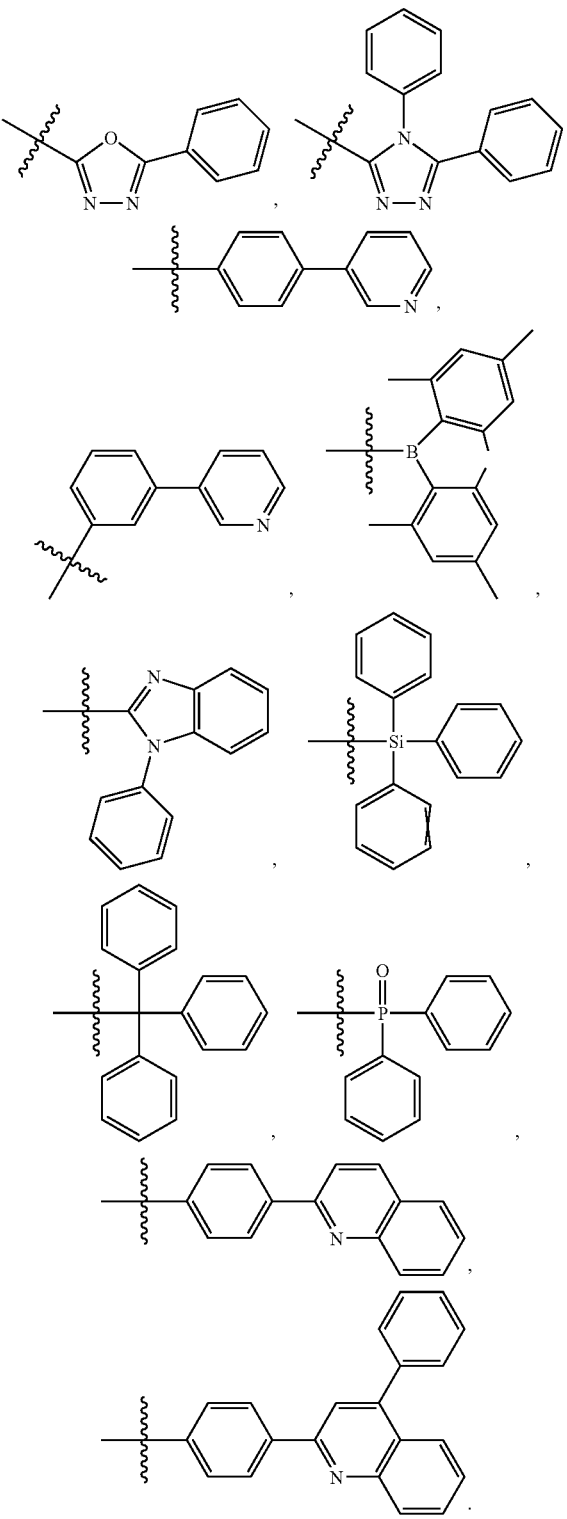

Referred to the formula of the phosphor material, at least one of $R^3$, $R^4$, and $R^5$ is not hydrogen atom. The C1-C22 halo-alkyl group is preferably independently selected from $CF_3$, $C_2F_5$. L of the mentioned formula is preferably selected from the group consisting of the following:

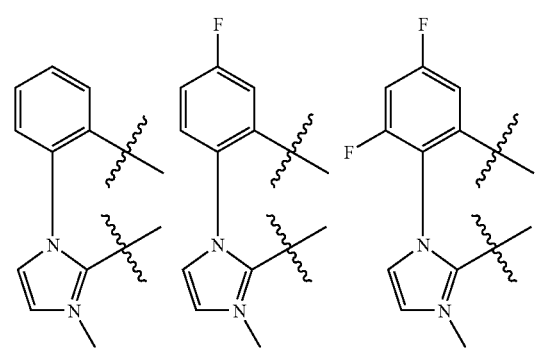
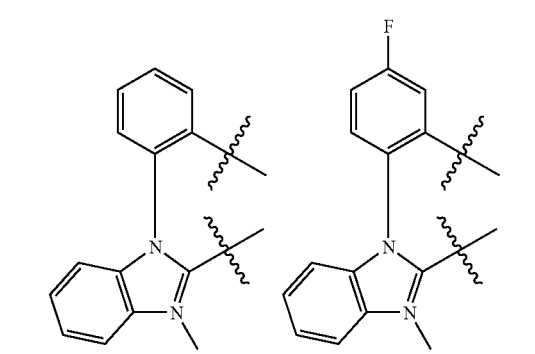
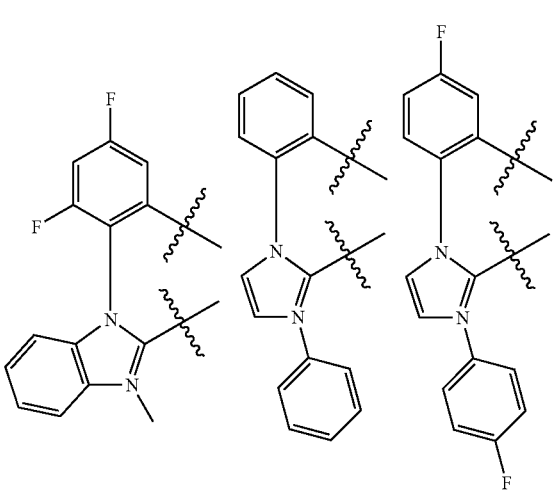
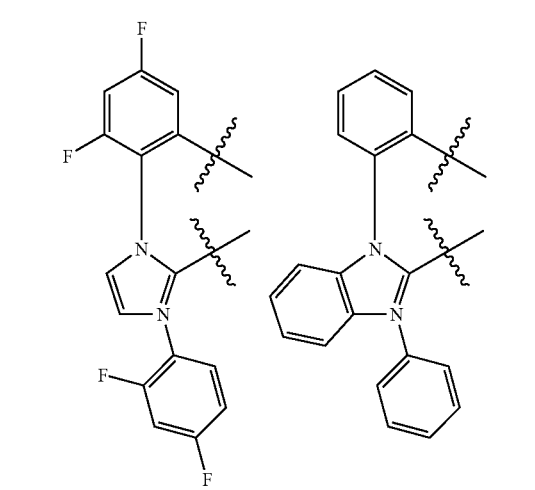
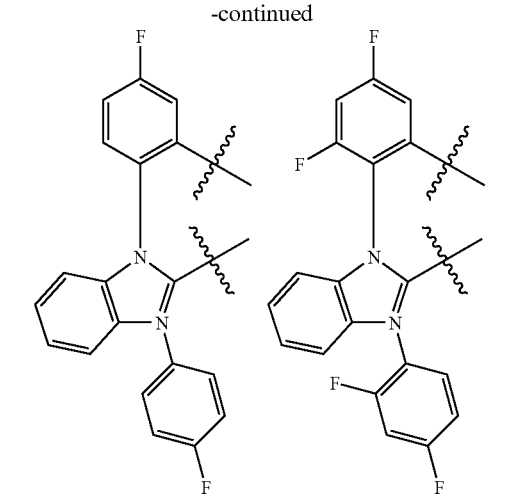
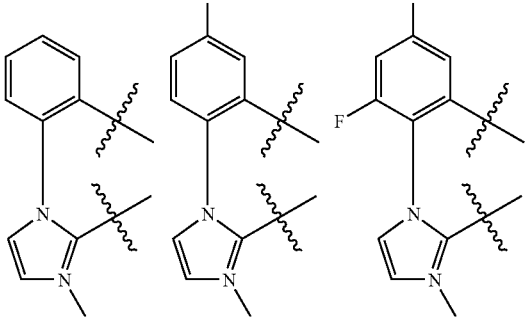
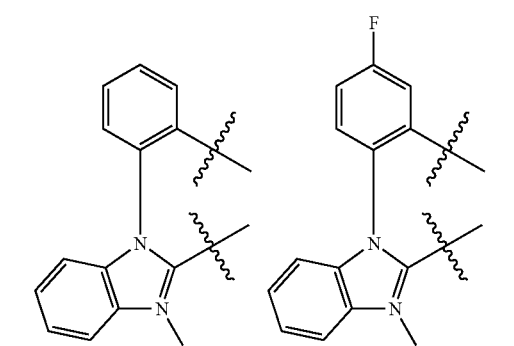
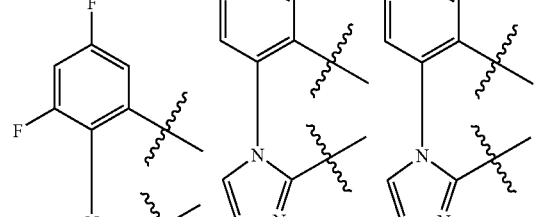
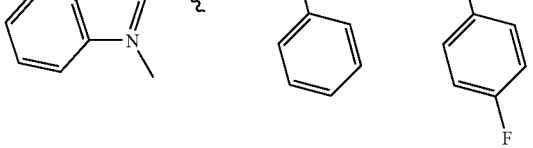

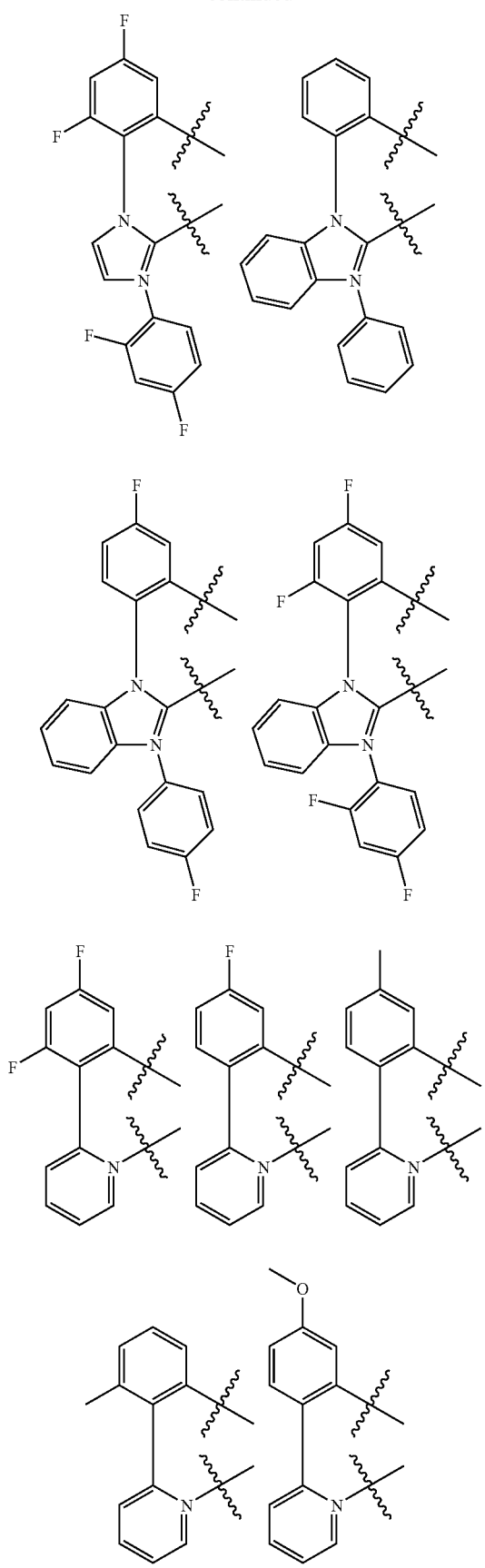
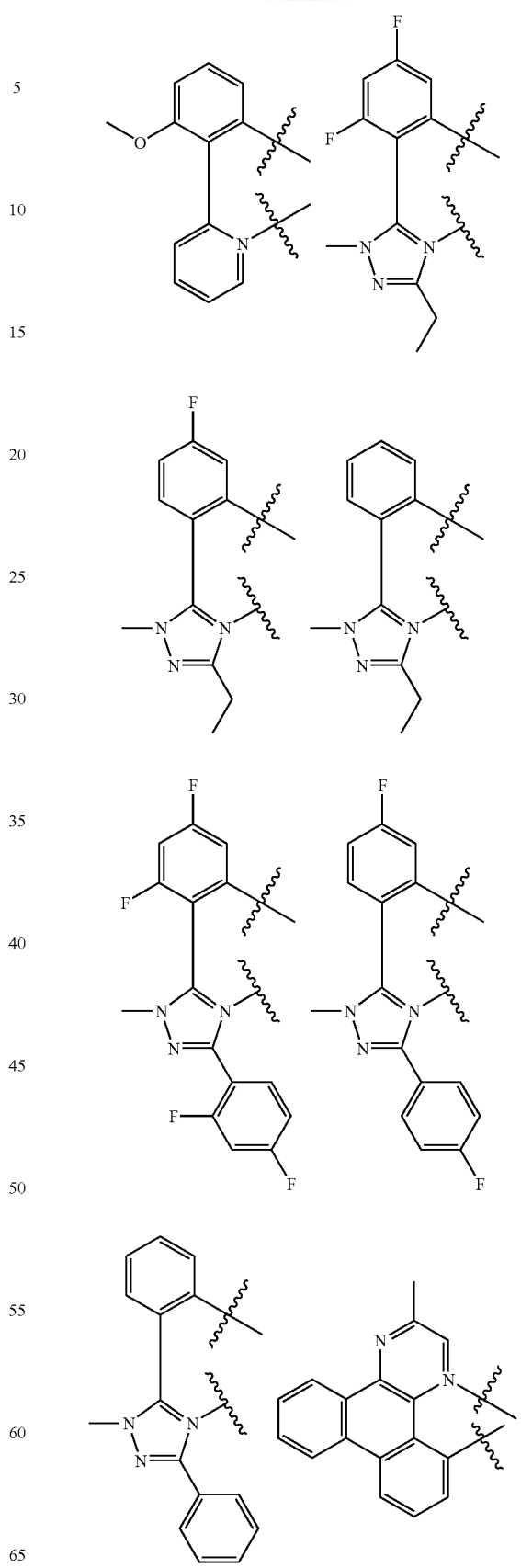

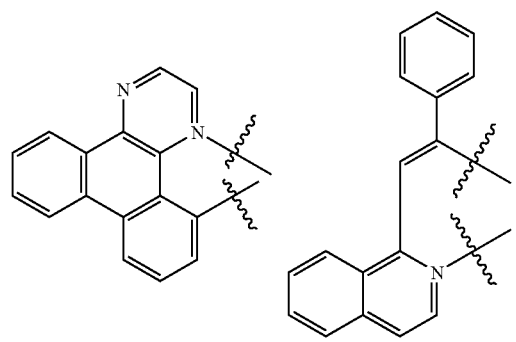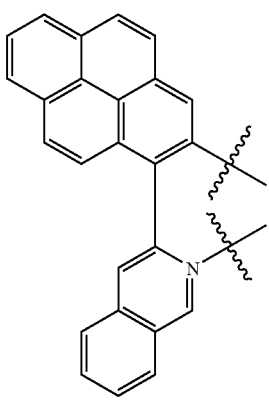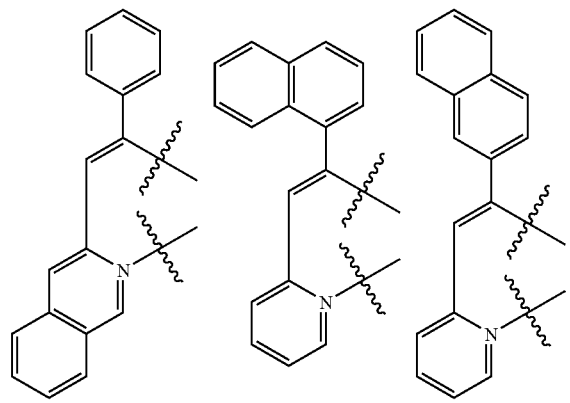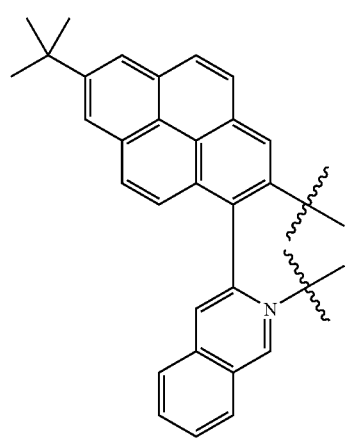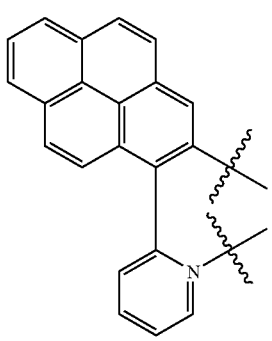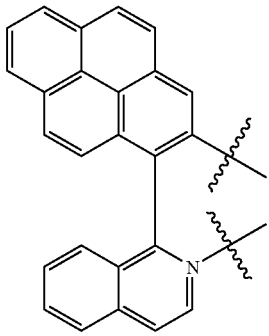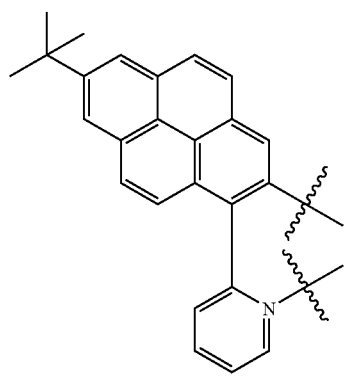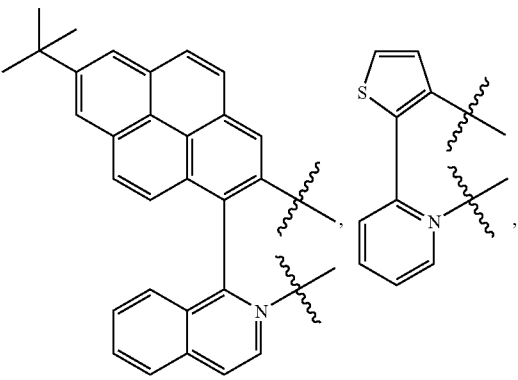

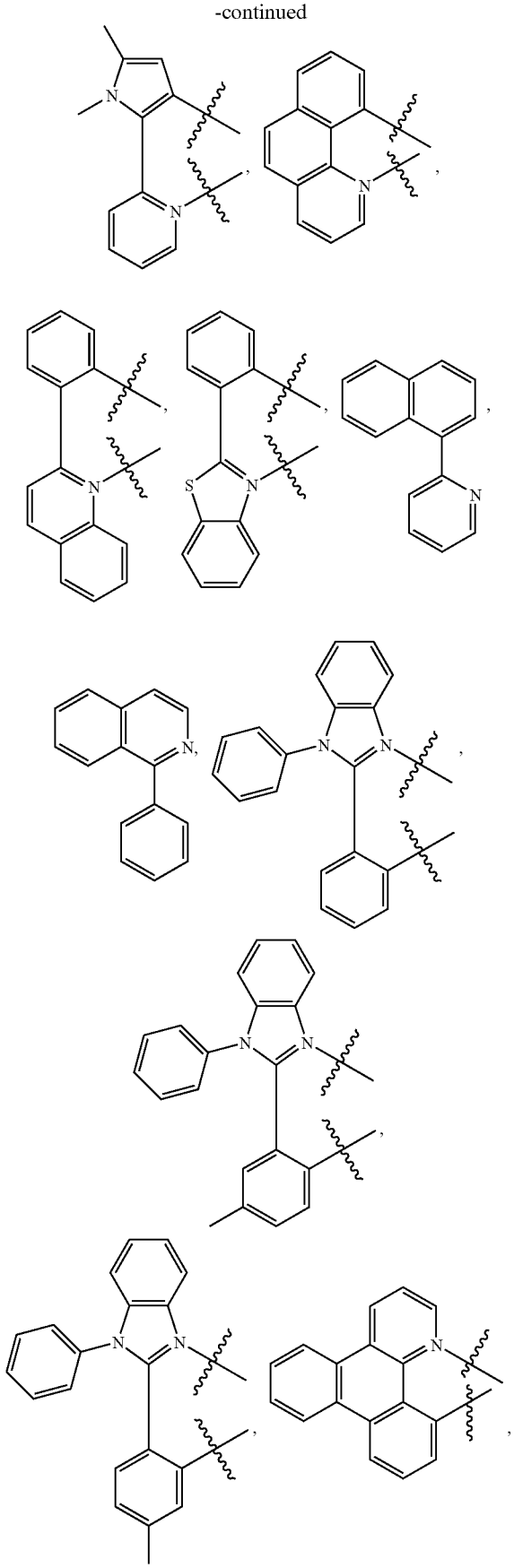

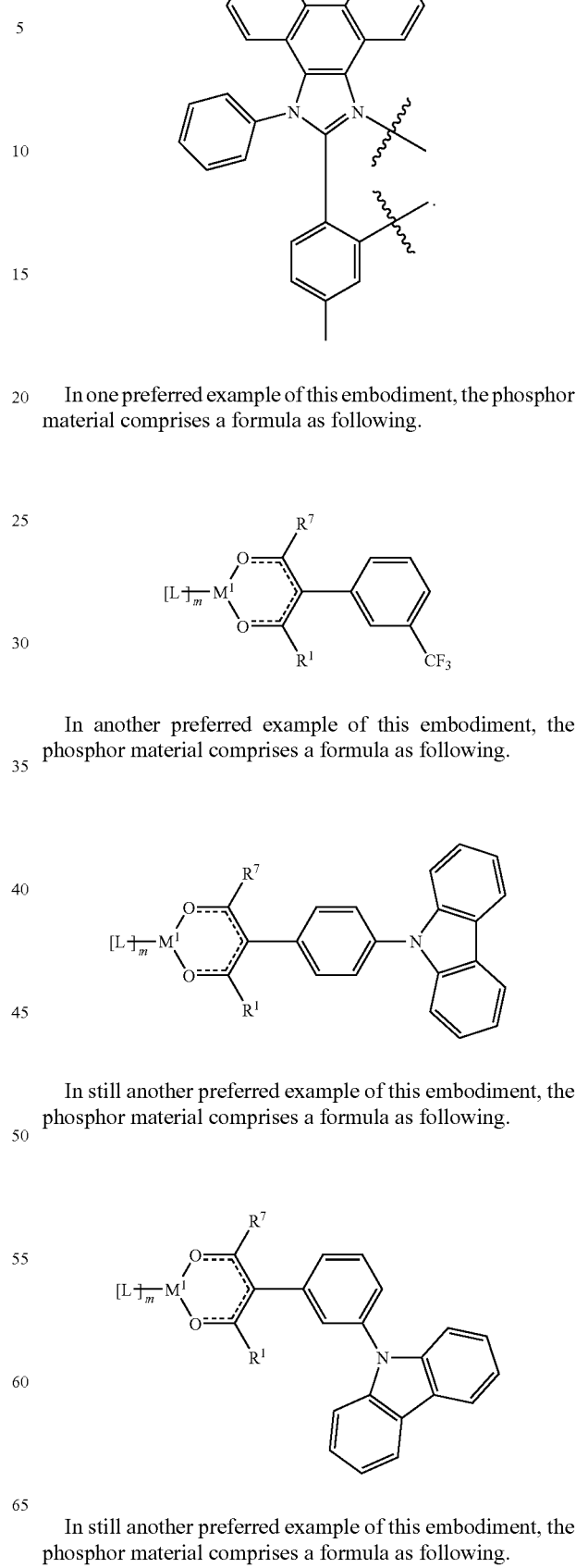

In one preferred example of this embodiment, the phosphor material comprises a formula as following.

In another preferred example of this embodiment, the phosphor material comprises a formula as following.

In still another preferred example of this embodiment, the phosphor material comprises a formula as following.

In still another preferred example of this embodiment, the phosphor material comprises a formula as following.

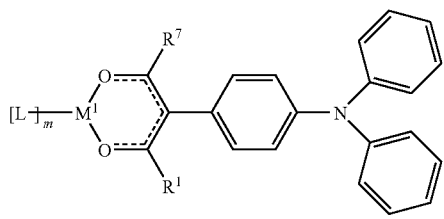

In still another preferred example of this embodiment, the phosphor material comprises a formula as following.

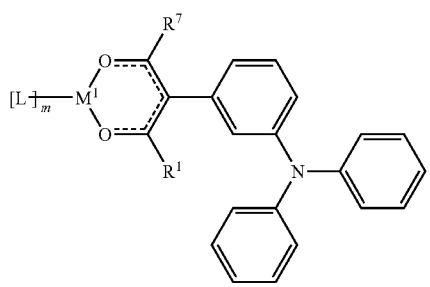

The second embodiment of this specification discloses a phosphor material with the following general formula.

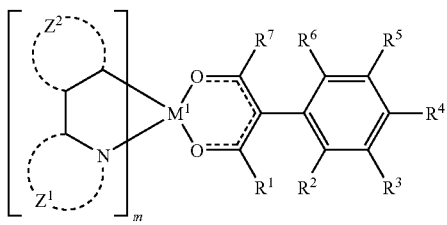

Referred to the general formula, $M^1$ is selected from Pt or Ir, and the value of m is 1 or 2. $R^1$ and $R^7$ can be identical or different. $R^1$ and $R^7$ can be independently selected from the group consisting of the following: H atom, halogen atom, C1-C22 alkyl group, and C1-C22 halo-alkyl group. $R^2$, $R^3$, $R^4$, $R^5$, and $R^6$ can be identical or different, and $R^2$, $R^3$, $R^4$, $R^5$, and $R^6$ are independently selected from the group consisting of the following: H atom, halogen atom, C1-C22 alkyl group, and C1-C22 halo-alkyl group, C6-C22 aryl group, and 5 to 7 members heterocyclic group with 1 to 4 heteroatom(s) selected from the group consisting of the following: N, O, B, P, and Si. The mentioned C6-C22 aryl group, and 5 to 7 members heterocyclic group(s) can be selected from one or the combination of the group consisting of the following.

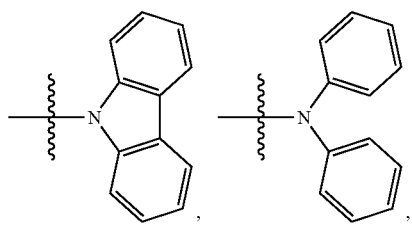

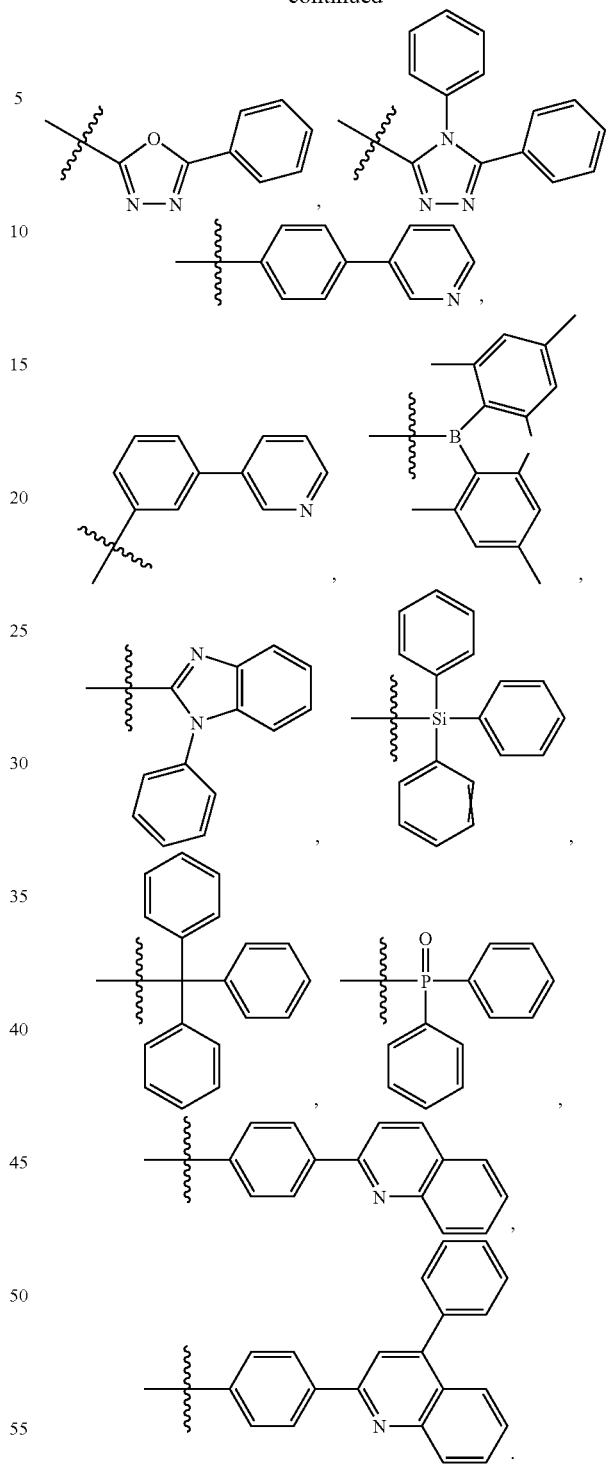

In the above-mentioned general formula, at least one of $R^3$, $R^4$, and $R^5$ is not H atom. $Z^1$ in the general formula represents a C3-C15 aromatic heterocyclic group with N atom(s), or a C3-C15 aromatic heterocyclic group with N atom(s) having at least one halo-substituent group(s), wherein can further comprises a nitrogen-containing single ring to nitrogen-containing fused rings wherein the number of the fused rings is not larger than 5. $Z^2$ represents a single ring or a fused ring wherein the fused ring comprises not larger than five rings.

According to this embodiment, each ring of $Z^2$ is selected from the group consisting of: a six member ring, a five member ring, a six member ring with at least one halo-substituent group(s), and a five member ring with at least one halo-substituent group(s).

Moreover, the phosphor material can be employed to form a phosphorescent emissive layer. That is, the components of the phosphorescent emissive layer can comprise the phosphor material according to this specification. According to this embodiment, the manufacture of the above-mentioned phosphorescent emissive layer comprising the phosphor material do not have to employ the doping process, so that the mentioned manufacture will be simplified. Preferably, when the luminance is equal to or larger than 500 cd/m², an OLED comprising the mentioned phosphorescent emissive layer can represent external quantum efficiency larger than or equal to 8 percent.

In another preferred example according to this embodiment, the phosphor material further comprises the structure as following.

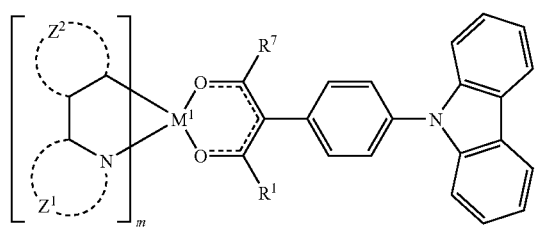

According to the mentioned example, the phosphor material can further comprise the following structures.

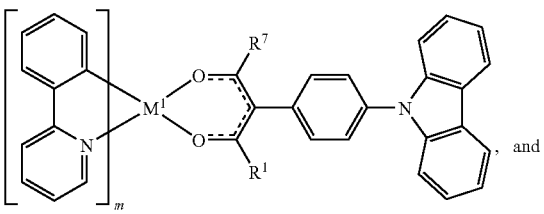
, and

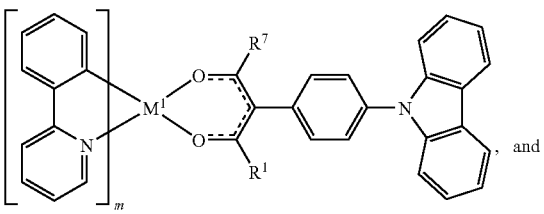

In still another preferred example of this embodiment, the mentioned phosphor material can further comprise the following structure.

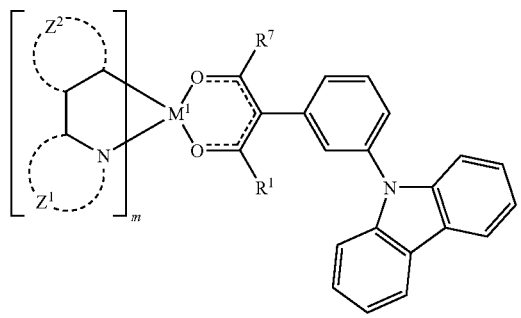

According to the mentioned example, the phosphor material can further comprise the following structures.

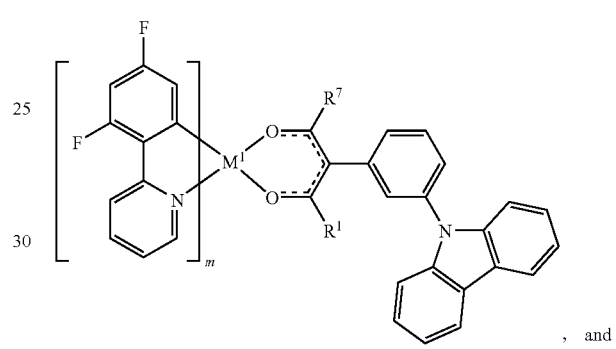
, and

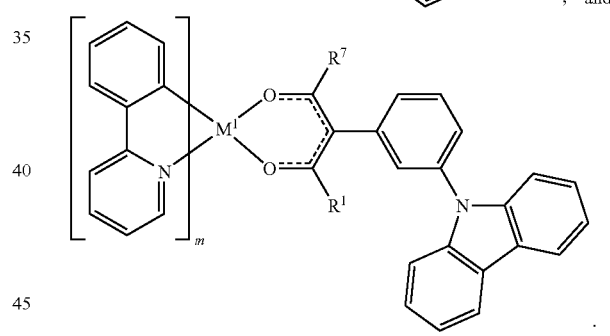

In still another preferred example of this embodiment, the mentioned phosphor material can further comprise the following structure.

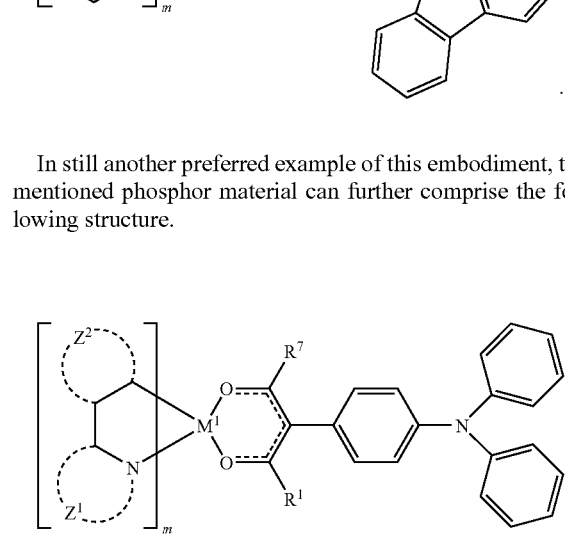

In still another preferred example of this embodiment, the mentioned phosphor material can further comprise the following structure.

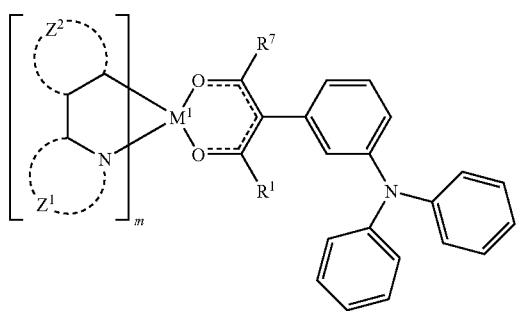

In still another preferred example of this embodiment, the mentioned phosphor material can further comprise the following structure.

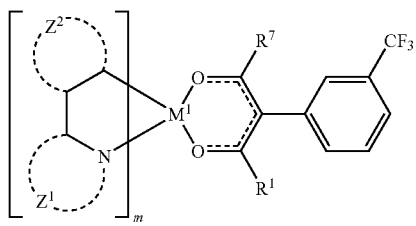

According to this example, the mentioned phosphor material can further comprise the following structure.

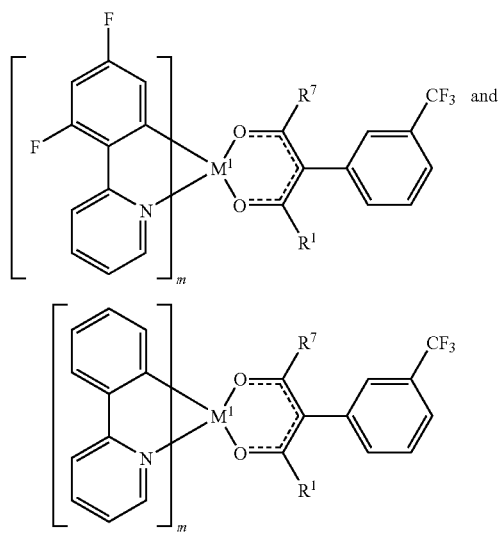

The third embodiment of this specification discloses an OLED, the OLED comprises one pair of electrodes, and at least one organic layer positioned between the electrodes, wherein the organic layer(s) comprise(s) an emissive layer. At least one layer of the organic layer(s) comprises a Pt or Ir complex, wherein the mentioned complex comprises an aryl substituted beta-diketone ancillary ligand. The general formula of the Pt (or Ir) complex is as following.

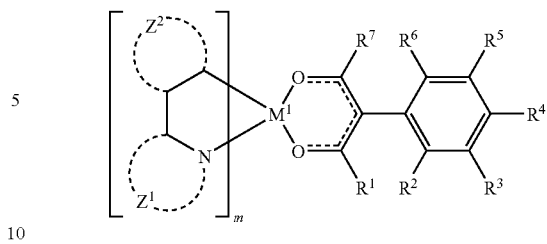

Referred to the above-mentioned general formula, $M^1$ is selected from Pt or Ir, and the value of m is 1 or 2. $R^1$ and $R^7$ can be identical or different, and $R^1$ and $R^7$ can be independently selected from the group consisting of the following: H atom, halogen atom, C1-C22 alkyl group, and C1-C22 halo-alkyl group. $R^2$, $R^3$, $R^4$, $R^5$, and $R^6$ can be identical or different, and $R^2$, $R^3$, $R^4$, $R^5$, and $R^6$ are independently selected from the group consisting of the following: H atom, halogen atom, C1-C22 alkyl group, and C1-C22 halo-alkyl group, C6-C22 aryl group, and 5 to 7 members heterocyclic group with 1 to 4 heteroatom(s) selected from the group consisting of the following: N, O, B, P, and Si. The mentioned C6-C22 aryl group or the heterocyclic group(s) can be independently selected from one or the combination of the group consisting of the following.

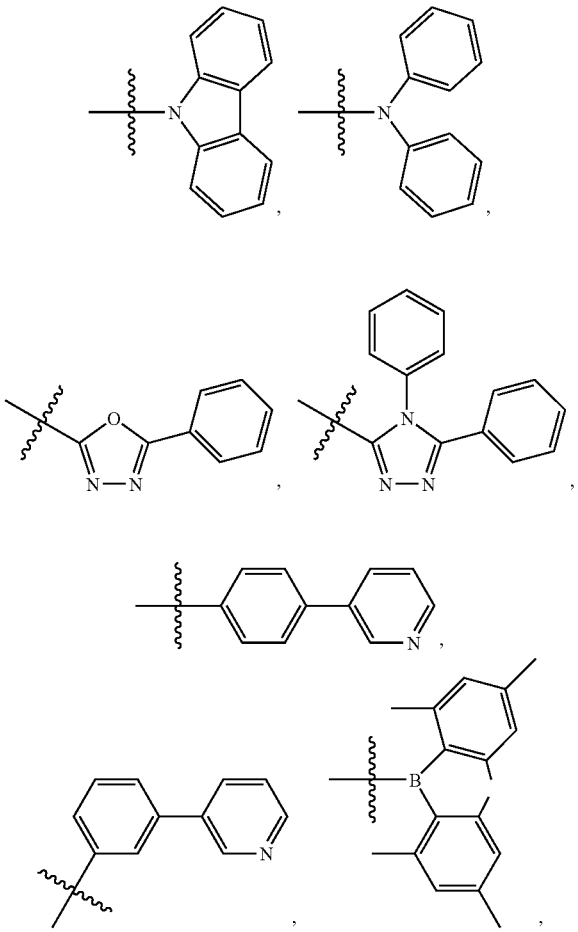

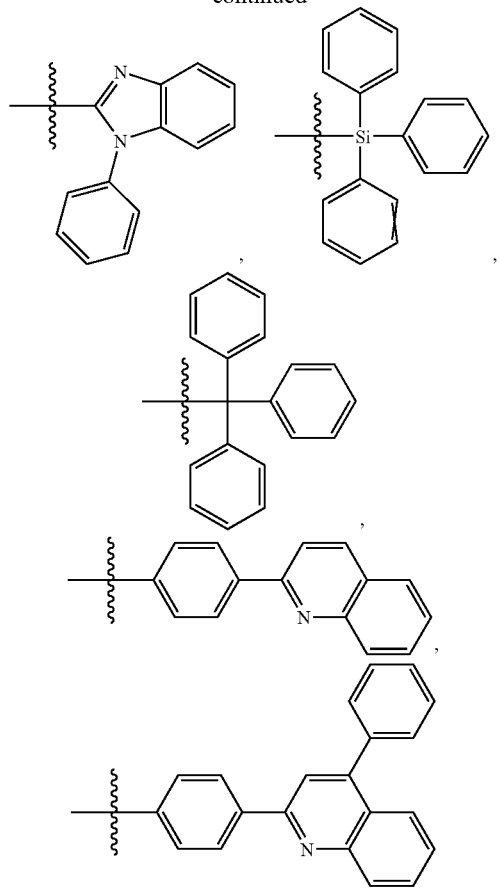

In the above-mentioned general formula, at least one of $R^3$, $R^4$, and $R^5$ is not H atom. $Z^1$ in the general formula represents C3-C15 aromatic heterocyclic group with N atom(s), or C3-C15 aromatic heterocyclic group with N atom(s) having at least one halo-substituent group(s), wherein $Z^1$ can further comprise a nitrogen-containing single ring to nitrogen-containing fused rings wherein the fused ring comprises not larger than five rings. $Z^2$ represents a single ring or a fused ring) wherein the fused ring comprises not larger than five rings. According to this embodiment, each ring of $Z^2$ is selected from the group consisting of: a six members ring, a five members ring, a six members ring with at least one halo-substituent group(s), and a five members ring with at least one halo-substituent group(s).

In one preferred example of this embodiment, the Pt (or Ir) complex can further comprise the following structure.

According to this example, the Pt (or Ir) complex can further comprise the following structure.

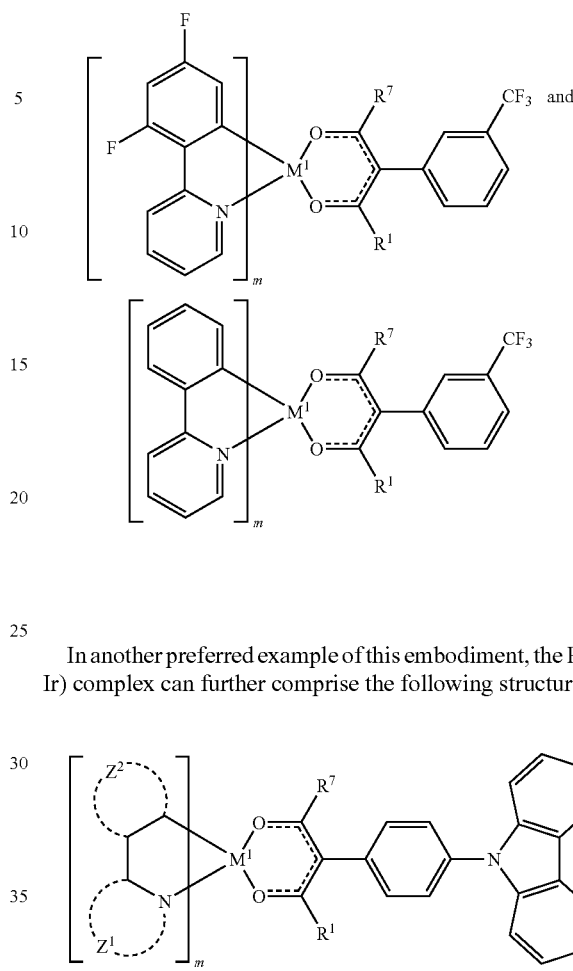

In another preferred example of this embodiment, the Pt (or Ir) complex can further comprise the following structure.

According to this example, the Pt (or Ir) complex can further comprise the following structures.

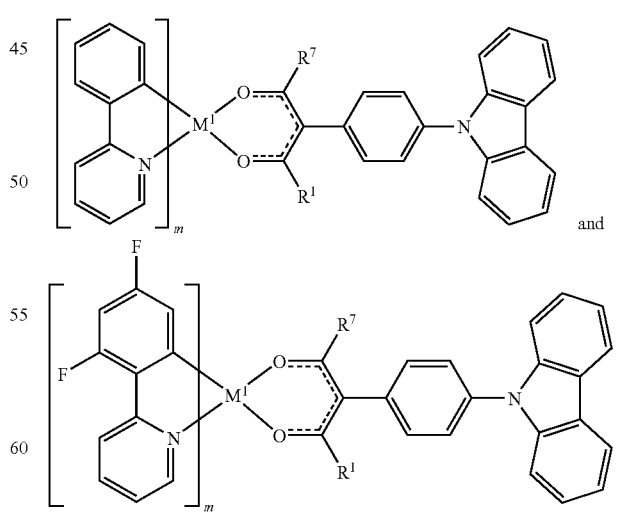

In still another preferred example of this embodiment, the Pt (or Ir) complex can further comprise the following structure.

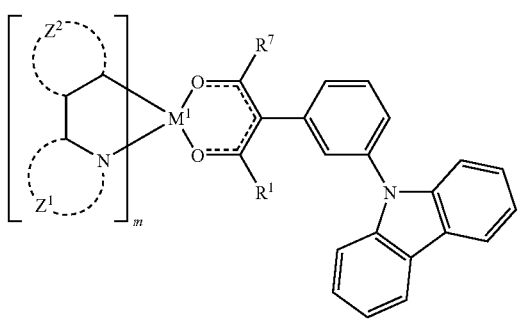

According to the mentioned example, the phosphor material can further comprise the following structures.

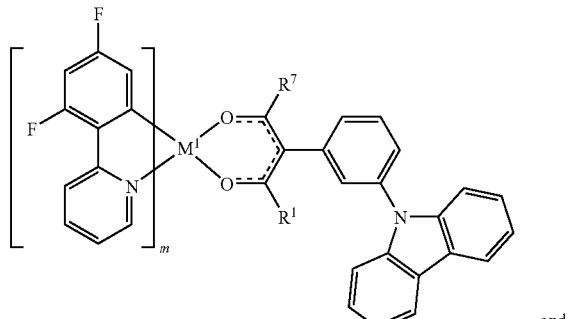

, and

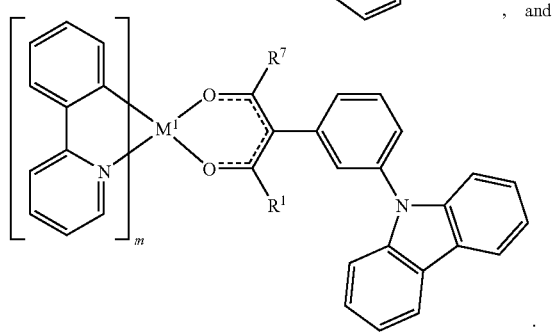

.

In still another preferred example of this embodiment, the Pt (or Ir) complex can further comprise the following structure.

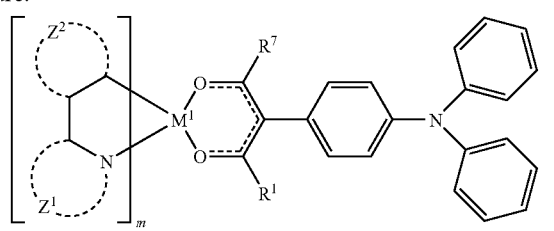

Example 1

3-(3-(trifluoromethyl)phenyl)pentane-2,4-dione

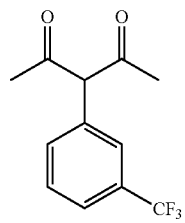 [SMILES: CC(=O)C(C(C)=O)c1cccc(C(F)(F)F)c1]

$^{1}$H NMR (400 M Hz, CDCl$_3$): δ 1.87 (s, 6H), 7.36 (d, 2H, J=7.2 Hz), 7.38 (s, 1H), 7.51 (t, 1H), 7.59 (d, 1H, J=7.2 Hz).

$^{13}$C NMR (100 M Hz, CDCl$_3$): δ 24.1 (CH3), 114.1 (C), 124.4 (C), 124.5 (C), 127.8 (C), 127.9 (C), 129.41 (C), 134.6 (C), 137.8 (C), 190.8 (C). HRMS (EI, m/z): calcd. for C$_{12}$H$_{11}$F$_3$O$_2$ 244.0711 found 244.0716 (M$^+$).

Example 2

3-(4-(9H-carbazol-9-yl)phenyl)pentane-2,4-dione

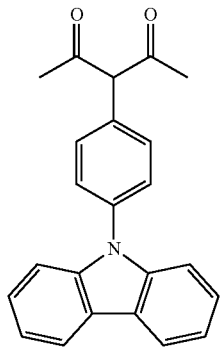 [SMILES: CC(=O)C(C(C)=O)c1ccc(-n2c3ccccc3c3ccccc32)cc1]

Yield: 82.2%. $^{1}$H NMR (400 M Hz, CDCl$_3$): δ 2.01 (s, 6H), 7.31 (t, 2H), 7.40-7.48 (m, 6H), 7.60 (d, 2H, J=8.4 Hz), 8.16 (d, 2H, J=8.4 Hz). $^{13}$C NMR (100 M Hz, CDCl$_3$): δ 24.3 (CH3), 109.7 (C), 114.5 (C), 120.1 (C), 120.4 (C), 123.5 (C), 126.0 (C), 127.3 (C), 132.6 (C), 136.1 (C), 137.1 (C), 140.7 (C), 191.0 (C). HRMS (EI, m/z): calcd for C$_{23}$H$_{19}$NO$_2$ 341.1416 found 341.1419 (M$^+$).

Example 3

3-(3-(9H-carbazol-9-yl)phenyl)pentane-2,4-dione

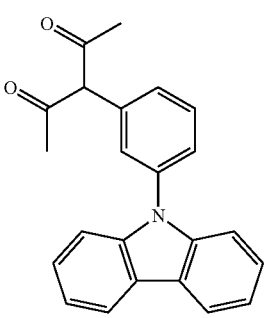 [SMILES: CC(=O)C(C(C)=O)c1cccc(-n2c3ccccc3c3ccccc32)c1]

Yield: 43.3%. $^{1}$H NMR (400 M Hz, CDCl$_3$): δ 2.03 (s, 6H), 7.29-7.33 (m, 3H), 7.38-7.45 (m, 5H), 7.57 (d, 2H, J=8.0 Hz), 7.64 (t, 1H), 8.15 (d, 2H, J=8.0 Hz). $^{13}$C NMR (100 M Hz, CDCl$_3$): δ 24.3 (CH3), 109.5 (C), 114.5 (CH), 120.2 (C), 120.5 (C), 123.5 (C), 126.0 (C), 126.3 (C), 129.6 (C), 130.2 (C), 138.2 (CH), 138.9 (CH), 140.7 (CH), 190.8 (C).

Example 4

Preparation of Platinum (II) (2-(4',6'-difluorophenyl)pyridinato-N,C2') (3-phenyl-2,4-pentanedionato-O,O) complex (Pt 1)

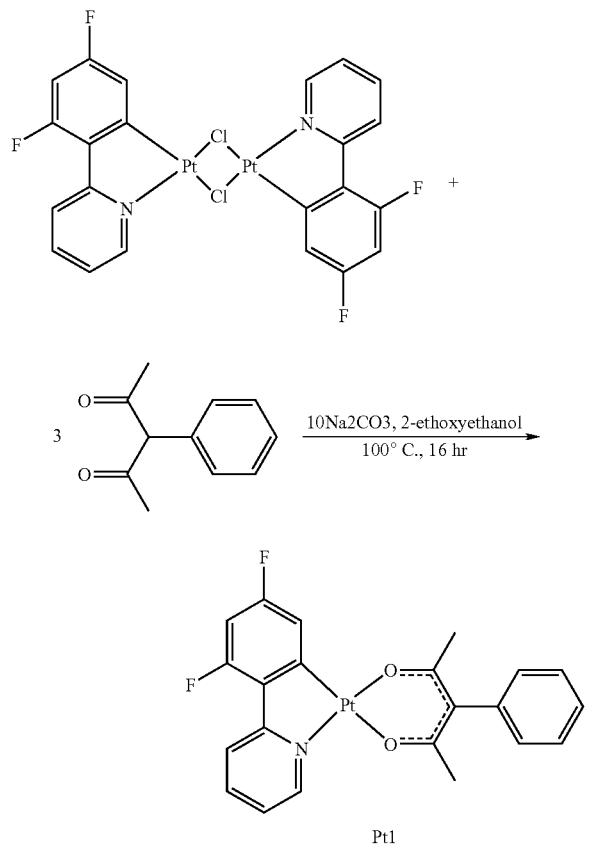

1.00 g dfppy-dimer (1.2 mmol), 0.613 g phenylpentane-2,4-dione (3.6 mmol), 1.24 g Na₂CO₃ (10 mmol), and 14 mL 2-ethoxylethanol are heated under Nitrogen for 16 hours at 100□. Then, the solvent is removed by reducing pressure, and the residue is dissolved in CH₂Cl₂. The product is dehydrated by magnesium sulfate, condensed, and purified by chromatography. After purification, the product is recrystallized with CH₂Cl₂/methanol, and the yield is 45.9%. The data of the Pt complex is as following.

¹H NMR (400 M Hz, CDCl₃): δ 1.76 (d, 6H, J=3.6 Hz), 6.57 (t, 1H), 7.10-7.20 (m, 4H), 7.27-7.31 (m, 1H), 7.35-7.39 (m, 2H), 7.83 (t, 1H), 7.97 (d, 1H, J=8.4 Hz), 9.01 (d, 1H, J=5.6 Hz). HRMS (EI, m/z): calcd for $C_{22}H_{17}F_2NO_2Pt$ 560.0875 found 560.0832 (M⁺). Anal. Calcd. for $C_{22}H_{17}F_2NO_2Pt$: C, 47.15; H, 3.06; N, 2.50%. Found: C, 47.32; H, 3.36; N, 2.69%.

Example 5

Preparation of Platinum (II) (2-(4',6'-difluorophenyl)pyridinato-N,C2') (3-(3-(trifluoromethyl)phenyl)-2,4-pentanedionato-O,O) complex (Pt 2)

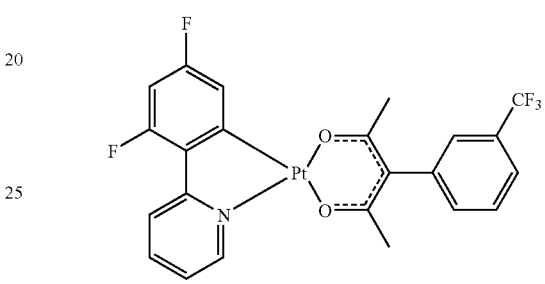

Yield: 58.7%. ¹H NMR (400 M Hz, CDCl₃): δ 1.73 (d, 6H, J=3.2 Hz), 6.57 (t, 1H), 7.07-7.15 (m, 2H), 7.39 (d, 1H, J=7.2 Hz), 7.48 (d, 1H, J=6.4 Hz), 7.52 (d, 2H, J=7.2 Hz), 7.57 (d, 1H, J=8.0 Hz), 7.84 (t, 1H), 7.97 (d, 1H, J=8.4 Hz), 8.96 (d, 1H, J=5.2 Hz). HRMS (EI, m/z): calcd for $C_{23}H_{16}F_5NO_2Pt$ 628.0749 found 628.0748 (M⁺). Anal. Calcd. for $C_{23}H_{16}F_5NO_2Pt$: C, 43.96; H, 2.57; N, 2.23%. Found: C, 43.90; H, 2.75; N, 1.86%.

Example 6

Preparation of Platinum (II) (2-(4',6'-difluorophenyl)pyridinato-N,C2') (3-(4-(9H-carbazol-9-yl)phenyl)-2,4-pentanedionato-O,O) complex (Pt 3)

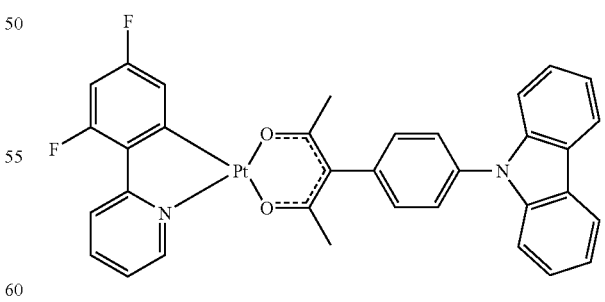

Yield: 37.1%. ¹H NMR (400 M Hz, CDCl₃): δ 1.90 (d, 6H, J=2.8 Hz), 6.59 (t, 1H), 7.13-7.17 (m, 2H), 7.29 (t, 1H), 7.40-7.46 (m, 6H), 7.59 (d, 2H, J=4.4 Hz), 7.85 (t, 1H), 7.99 (d, 1H, J=8.4 Hz), 8.15 (d, 1H, J=7.6 Hz), 9.02 (d, 1H, J=5.2 Hz). HRMS (EI, m/z): calcd for $C_{34}H_{24}F_2N_2O_2Pt$ 725.1454 found 725.1452 (M⁺).

Example 7

Preparation of Platinum (II) (2-(4',6'-difluorophenyl)pyridinato-N,C2') (3-(3-(9H-carbazol-9-yl)phenyl)-2,4-pentanedionato-O,O) complex (Pt 4)

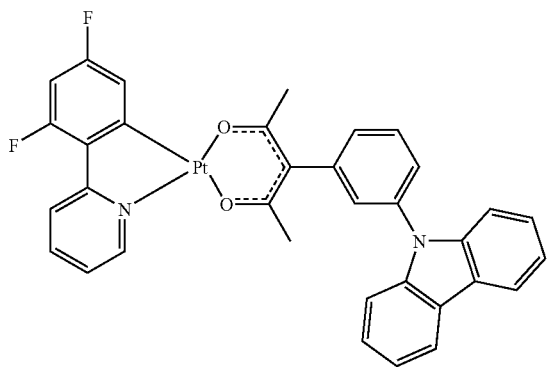

Yield: 18.4%. $^1$H NMR (400 M Hz, CDCl$_3$): δ 1.91 (d, 6H, J=2.8 Hz), 6.57 (t, 1H), 7.10-7.15 (m, 2H), 7.27-7.32 (m, 3H), 7.40-7.44 (m, 5H), 7.54 (d, 1H, J=8.0 Hz), 7.63 (t, 1H), 7.83 (t, 1H), 7.96 (d, 1H, J=8.0 Hz), 8.14 (d, 1H, J=3.6 Hz), 8.98 (d, 2H, J=5.6 Hz).

Example 8

Preparation of Platinum (II) (2-phenylpyridinato-N, C2') (3-phenyl-2,4-pentanedionato-O,O) complex (Pt 1)

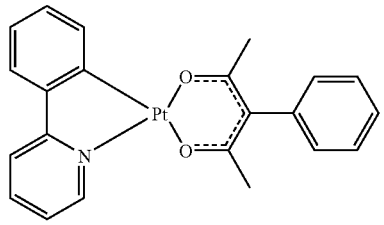

Yield: 40.0%. $^1$H NMR (400 MHz, CDCl$_3$): δ 1.89 (s, 6H), 7.09-7.14 (m, 2H), 7.21 (t, 1H, J=Hz), 7.29 (t, 1H, J=7.2 Hz), 7.40-7.47 (m, 2H), 7.58 (d, 1H, J=8.4 Hz), 7.65 (t, 1H), 7.81 (t, 1H, J=8.0 Hz), 8.14 (d, 2H, J=8.0 Hz), 9.01 (d, 1H, J=5.6 Hz).

Example 9

Preparation of Platinum (II) (2-phenylpyridinato-N, C2') (3-(4-(9H-carbazol-9-yl)phenyl)-2,4-pentanedionato-O,O) complex

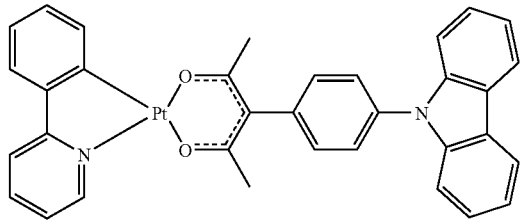

Yield: 40.0%. $^1$H NMR (400 MHz, CDCl$_3$): δ 1.89 (s, 6H), 7.09-7.14 (m, 2H), 7.21 (t, 1H, J=Hz), 7.29 (t, 1H, J=7.2 Hz), 7.40-7.47 (m, 2H), 7.58 (d, 1H, J=8.4 Hz), 7.65 (t, 1H), 7.81 (t, 1H, J=8.0 Hz), 8.14 (d, 2H, J=8.0 Hz), 9.01 (d, 1H, J=5.6 Hz).

Example 10

Preparation of Iridium (III) bis(2-phenylpyridinato-N,C2') (3-phenyl-2,4-pentanedionato-O,O) (Ir(PPy)$_2$(phacac))

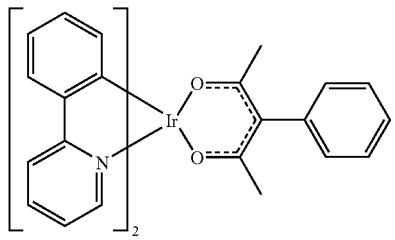

Yield: 35.2%. $^1$H NMR (400 MHz, CDCl$_3$): δ 1.50 (s, 6H), 6.26 (d, 1H, J=7.6 Hz), 6.68 (t, 1H), 6.80 (t, 1H), 7.08 (d, 1H, J=7.2 Hz), 7.18-7.30 (m, 9H), 7.55 (d, 2H, J=8.4 Hz), 7.76 (t, 2H), 7.86 (d, 2H, J=8.0 Hz), 8.64 (d, 2H, J=5.2 Hz). HRMS (FAB, m/z): calcd for C$_{33}$H$_{27}$IrN$_2$O$_2$ 676.1702 found 676.1711 (M$^+$).

Example 11

Optical Property of Platinum Complexes

FPt [platinum(II) (4',6'-difluorophenylpyridinato-N,C2') (2,4-pentanedionato-O,O)] is a phosphorescent emission material with acetylacetonate ligand. The Pt complexes (Pt 1, Pt 2, Pt 3) disclosed in this specification comprise aryl-modified acetylacetone ligand(s). The general formula of FPt is:

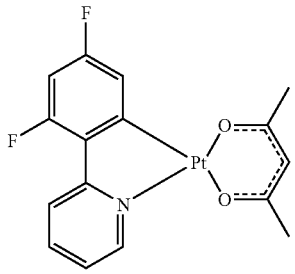

FIG. 1A is a diagram of Photoluminescence (PL) of FPt and Pt complexes (Pt 1, Pt 2, and Pt 3) in diluted dichloromethane solution at room temperature. As presented in FIG. 1A, the photoluminescent (PL) spectra showed nearly identical structured monomer emission. This finding indicates that the aryl substituents on the acetylacetonate ligand do not interfere the emission spectra thereof in the diluted solution.

Example 12

Optical Property of Iridium Complexes

Figure 1B:
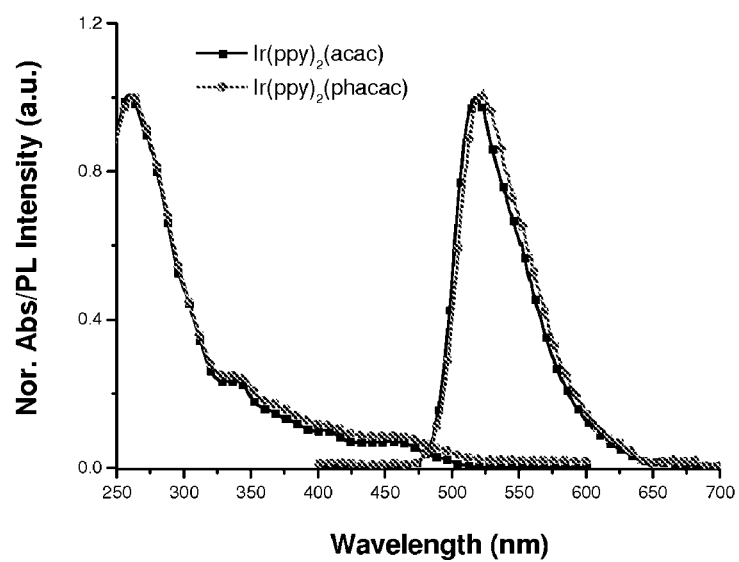
FIG. 1B depicts illustrates the Photoluminescence spectra of Ir complexes ($Ir(PPy)_2(acac)$ and $Ir(PPy)_2(phacac)$) in diluted solution at room temperature.

FIG. 1B represents the PL spectra of the Ir complex, Iridium (III) bis(2-phenylpyridinato-N, C2') (2,4-pentanedionato-O,O) (hereinafter called Ir(PPy)$_2$(acac) and Ir(PPy)$_2$(phacac). The formula of Ir(PPy)$_2$(acac) is as following. The PL spectra of these two Ir complexes are the same, too. Therefore, the aryl modification on the beta-diketone ligand of the mentioned formula will not affect the emission spectral position of a complex in diluted solution.

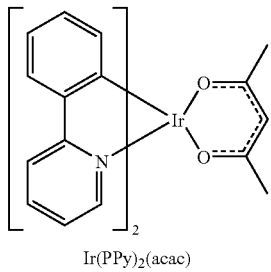

Ir(PPy)$_2$(acac)

Example 13

Employing Pt Complexes as the Dopants in Emissive Layer of OLEDs

Figure 2A:
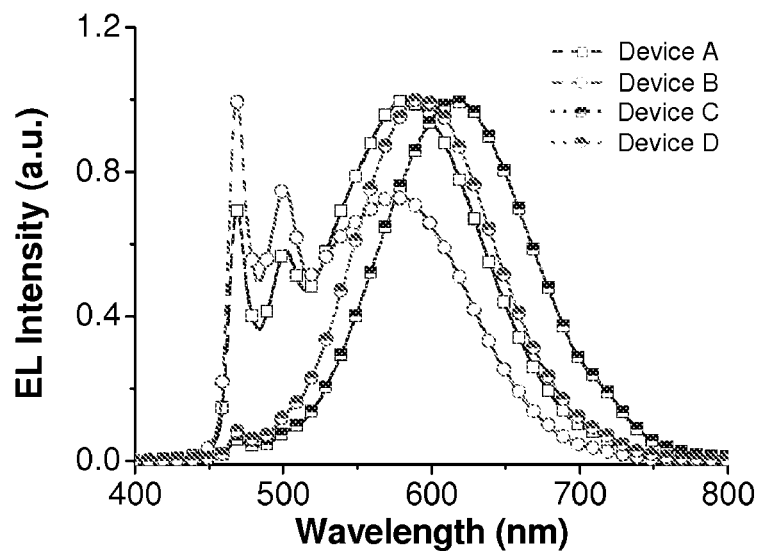
FIG. 2A shows the electroluminescence (EL) spectra of the Devices A to D.
Figure 2B:
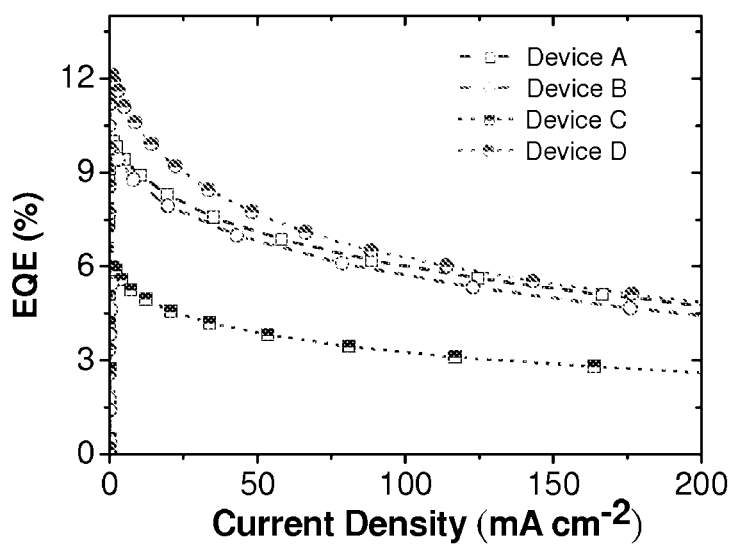
FIG. 2B shows the external quantum efficiency (EQE)-current density characteristics of the Devices A to D.

In the devices A to D, FPt and Pt 1 are employed as the dopants in the light emissive layers of OLEDs. As shown in FIG. 2A, whitish light was obtained when the doping concentration of FPt and Ph-FPt in host at 15%, and their EL spectra showed identical monomer emission peaks at 469 and 501 nm accompanied with different aggregrated broadband emissions at 582 and 575 nm, respectively. These two devices exhibited similar peak EQEs of ca.10%. When the doping concentration raised to 50%, the EL spectra were mainly dominated by the broadband emission at 617 and 592 nm together with peak EQE of 6.02% and 12.4%, respectively, for the FPt- and Pt 1-doped devices. As shown in FIG. 2B, there is a significant decrease of EQE in the FPt-doped devices as doping concentration increased from 15% to 50%.

Example 14

Figure 3A:
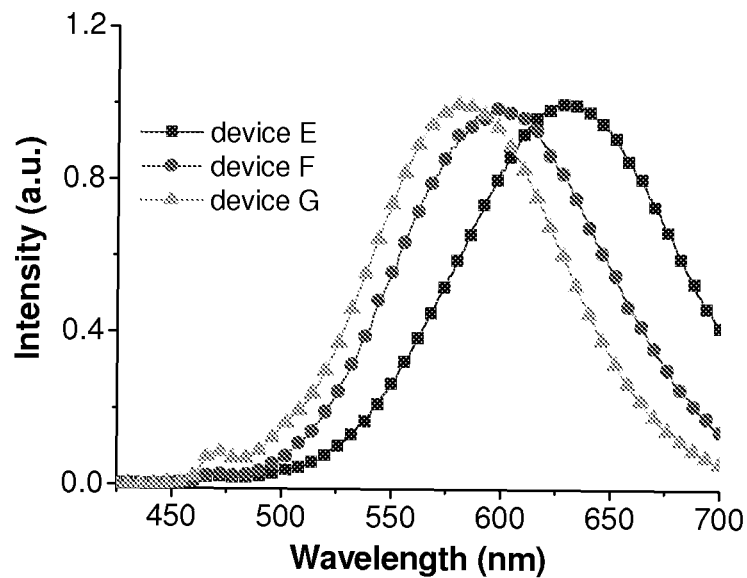
FIG. 3A shows the electroluminescence (EL) spectra of the Devices E to G.
Figure 3B:
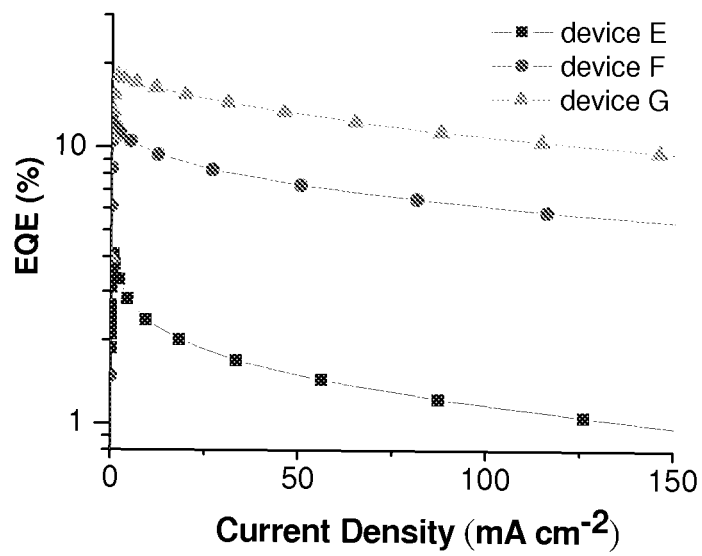
FIG. 3B the external quantum efficiency (EQE)-current density characteristics of the Devices E to G.

Employing Pt Complexes in the Non-Doped Phosphorescent Emissive Layers of Monochromatic OLEDs In the devices E to G, FPt and Pt complexes (Pt 1 and Pt 3) are employed as the non-doped orange emissive layer of OLEDs. As shown in FIG. 3A, the aggregrated broadband emissions of devices E-G are blue-shift of the luminescence spectrum as the size of the aryl substituent being larger. As shown in FIG. 3B, as in neat film state, the peak EQE of the FPt-based devices (device E) further drop to 4.08% while that of the Pt 1- and Pt 2-based devices (devices F and G) were retained in high levels of 11.9% and 18.0%, respectively (FIG. 3B). In addition to the higher EQEs, the efficiency roll-off at high current density was apparently suppressed in devices F and G relative to device E.

Example 15

Figure 4A:
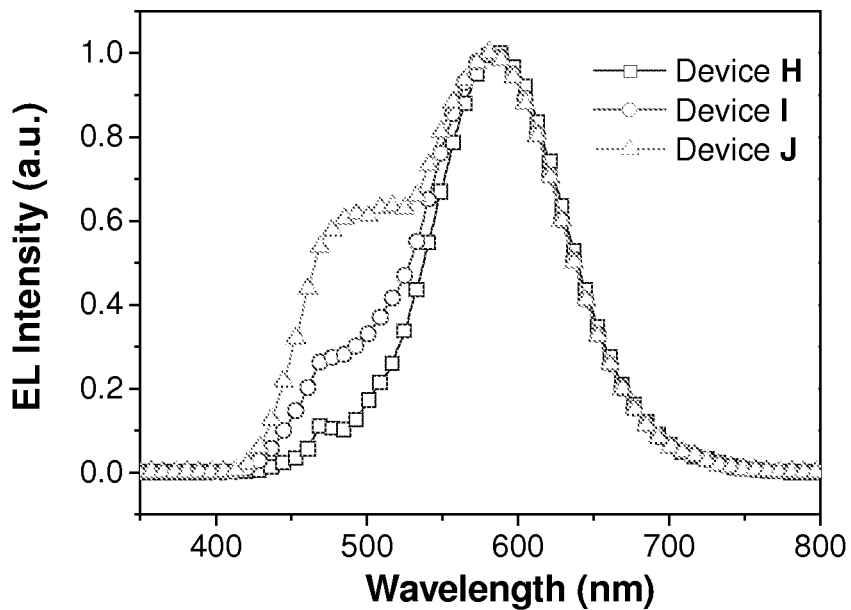
FIG. 4A shows the electroluminescence (EL) spectra of the Devices H to J.
Figure 4B:
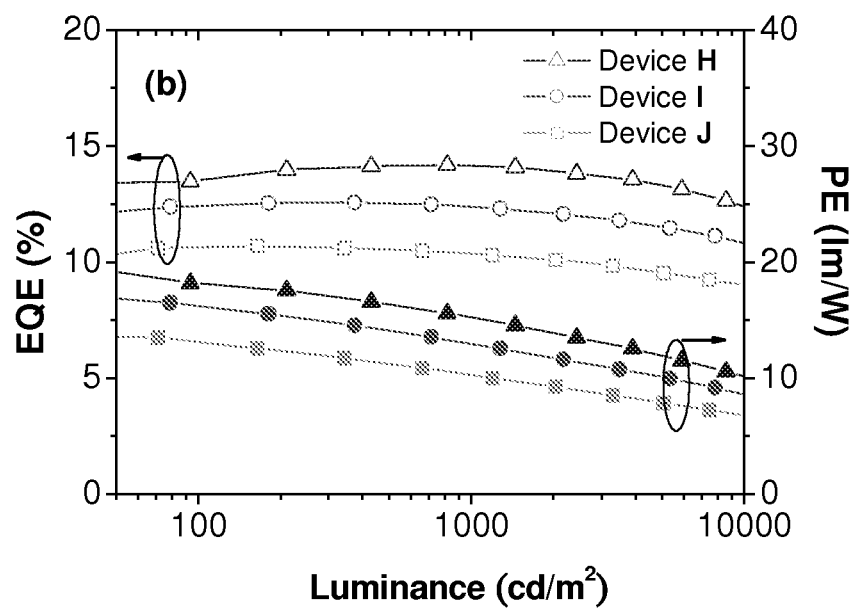
FIG. 4B shows the external quantum efficiency (EQE)-luminance-powder efficiency (PE) characteristics of the Devices H to J.

Employing Pt Complexes as the Non-Doped Phosphorescent Emissive Layers of White OLEDs In devices H to J, we slightly modified the structure of the monochromatic device G (see Table 1 for detailed device structures) and decreased mCP layer thickness to let exciton recombination taken place in the non-doped blue fluorescence PPP (1-(4-(1-pyrenyl)phenyl)pyrene) layer. Besides, NPB (N,N'-bis(naphthalen-1-yl)-N,N'-bis(phenyl)-benzidine) barrier layer was introduced to prevent electron and exaciton quenching at the ITO anode. As illustrated in FIG. 4A, when the thickness of mCP layer reduced, the blue fluorescence originated from PPP layer became more pronounced. White EL with appropriate CRI was obtained when mCP layer thickness were 3 nm and 2 nm for devices I and J, respectively. The maximum EQE and PE of devices I/J were 12.5/10.6% and 17.8/13.6 μm/W with CRI value of 66 and 73, respectively. Moreover, the presented WOLEDs showed a quite flat response of EQE with respect to luminescence over a wide range (FIG. 4B). At a high luminescence of 5000 cd/m2, the EQE of devices I/J slightly decreased to 11.5/9.6% which is even higher than that of highly efficient doped WOLEDs operated under similar brightness condition. The presented WOLEDs I/J are the first non-doped device realizing incandescent bulb efficiency (10~15 μm/W) even at high luminescence levels.

TABLE 1

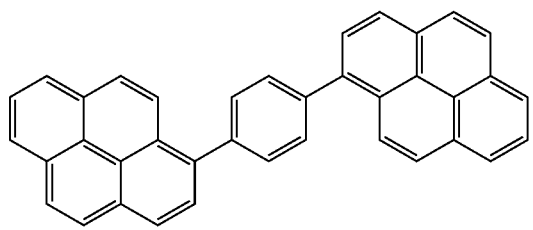

PPP

| Device structure [a] | V (V) | EQE (%) | CE (cd/A) | PE (lm/W) | $\lambda_{max}$ (nm) [c] | CIE (x, y) [c] | CRI [c] |
|---|---|---|---|---|---|---|---|
| | | | At ca. 500 cd/m² [b] | | | | |
| A ITO/PPP (40 nm)/mCP (10 nm)/ 15% FPt in mCP (25 nm)/BCP (40 nm)/LiF (1 nm)/Al | 7.2 | 9.9 | 26.3 | 11.5 | 582 | (0.42, 0.45) | 70 |
| B ITO/PPP (40 nm)/mCP (10 nm)/ 15% Pt1 in mCP (25 nm)/BCP (40 nm)/ LiF (1 nm)/Al | 7.7 | 9.5 | 25.8 | 10.5 | 467 | (0.37, 0.44) | 71 |
| C ITO/PPP (40 nm)/mCP (10 nm)/50% FPt in mCP (25 nm)/BCP (40 nm)/LiF (1 nm)/Al | 8.8 | 5.7 | 11.5 | 4.1 | 617 | (0.54, 0.43) | □- |

TABLE 1-continued

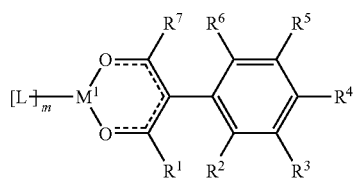

PPP

| Device structure [a] | At ca. 500 cd/m² [b] | | | | | | |
|---|---|---|---|---|---|---|---|
| | V (V) | EQE (%) | CE (cd/A) | PE (lm/W) | $\lambda_{max}$ (nm) [c] | CIE (x, y) [c] | CRI [c] |
| D ITO/PPP (40 nm)/mCP (10 nm)/50% Pt1 in mCP (25 nm)/BCP (40 nm)/ LiF (1 nm)/Al | 8.0 | 12.0 | 31.3 | 12.4 | 592 | (0.51, 0.47) | □- |
| E ITO/PPP (40 nm)/mCP (10 nm)/FPt (25 nm)/BCP (40 nm)/LiF (1 nm)/Al | 10.4 | 2.1 | 3.1 | 1.0 | 630 | (0.58, 0.41) | □- |
| F ITO/PPP (40 nm)/mCP (10 nm)/ Pt1 (20 nm)/BCP (40 nm)/LiF (1 nm)/Al | 8.8 | 11.4 | 27.4 | 9.7 | 600 | (0.52, 0.46) | □- |
| G ITO/PPP (40 nm)/mCP (10 nm)/ Pt3 (20 nm)/BCP (40 nm)/LiF (1 nm)/Al | 6.2 | 16.5 | 48.9 | 24.7 | 583 | (0.48, 0.49) | □- |
| H ITO/NPB (20)/PPP (30 nm)/mCP (4 nm)/ Pt3 (20 nm)/BCP (40 nm)/LiF (1 nm)/Al | 7.6 | 14.1 | 39.5 | 16.4 | 586 | (0.48, 0.47) | 59 |
| I ITO/NPB (20)/PPP (30 nm)/mCP (3 nm)/ Pt3 (20 nm)/BCP (40 nm)/LiF (1 nm)/Al | 7.7 | 12.5 | 34.5 | 14.2 | 583 | (0.44, 0.46) | 66 |
| J ITO/NPB (20)/PPP (30 nm)/mCP (2 nm)/ Pt3 (20 nm)/BCP (40 nm)/LiF (1 nm)/Al | 7.7 | 10.6 | 27.8 | 11.3 | 580 | (0.39, 0.43) | 73 |

[a] PPP (1-(4-(1-pyrenyl)phenyl)pyrene) and BCP (2,9-dimethyl-4,7-diphenyl-1,10-phenanhroline) served as the hole and electron transport layers, respectively, mCP (N,N'-dicarbazolyl-3,5-benzene) served as electron blocking and host materials, and LiF acted as electron injection layer.
[b] The data for voltage (V), external quantum efficiency (EQE), current efficiency (CE) and powder efficiency (PE) obtained at 500 cd/m².
[c] The data were taken at 9 V.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A phosphor material, comprising:
a transition metal $M^1$, wherein $M^1$ is Pt or Ir; and
an aryl substituted beta-diketone ancillary ligand;
wherein a general formula of the phosphor material is as the following,

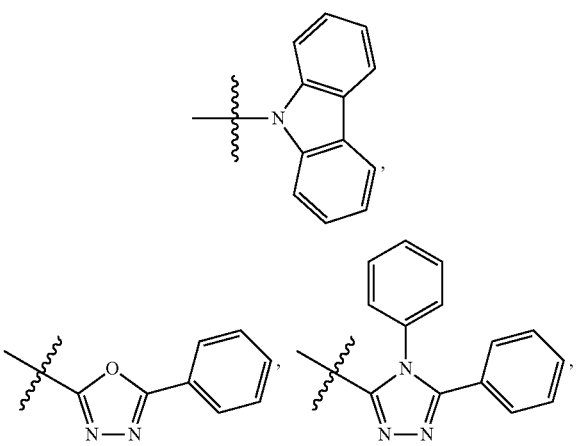

wherein L is a ligand; wherein m is 1 or 2; wherein $R^1$ and $R^7$ can be identical or different, and $R^1$ and $R^7$ are independently selected from the group consisting of the following: H atom, halogen atom, C1-C6 alkyl group, and C1-C6 haloalkyl group; wherein $R^2$, $R^3$, $R^4$, $R^5$, and $R^6$ can be identical or different, and $R^2$, $R^3$, $R^4$, $R^5$, and $R^6$ are independently selected from the group consisting of the following: H atom, halogen atom, C1-C22 alkyl group, C1-C22 haloalkyl group, and C6-C22 aryl group or 5 to 7 membered heterocyclic group with 1 to 4 heteroatom(s) selected from N, O, B, P, Si; wherein the C6-C22 aryl group or 5 to 7 membered heterocyclic group is selected from the group consisting of the following:

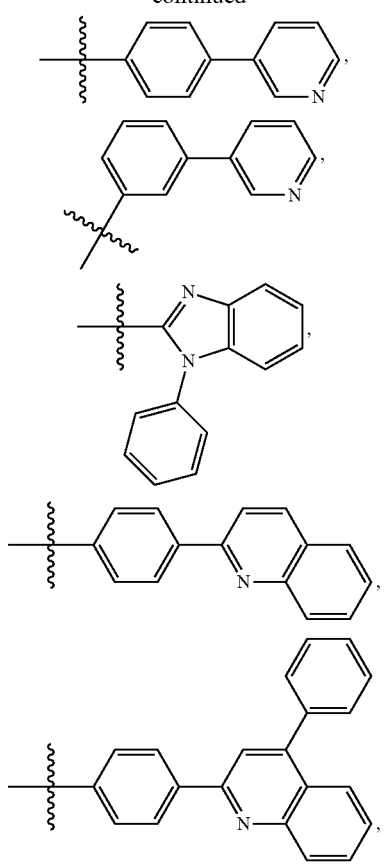
wherein at least one of $R^3$, $R^4$, and $R^5$ is not H atom;
wherein L is selected from the group consisting of the following:
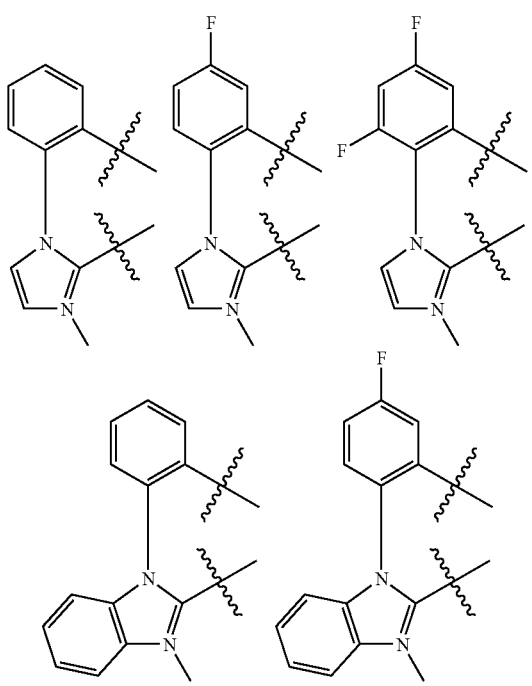
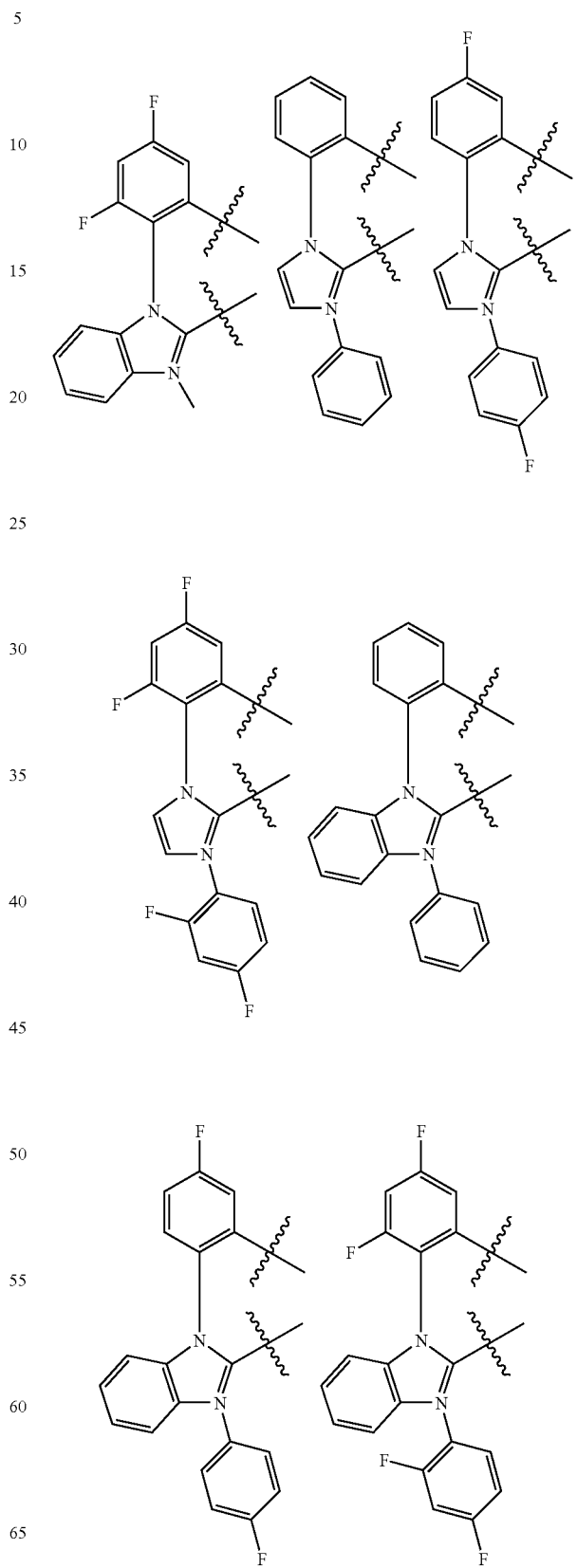

-continued
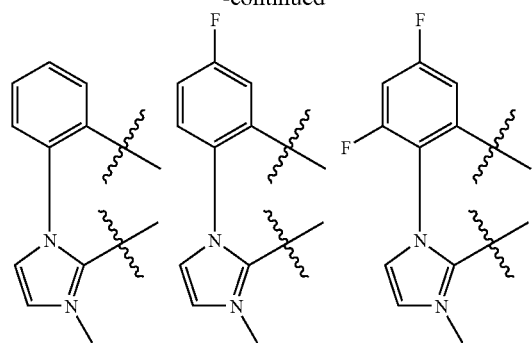
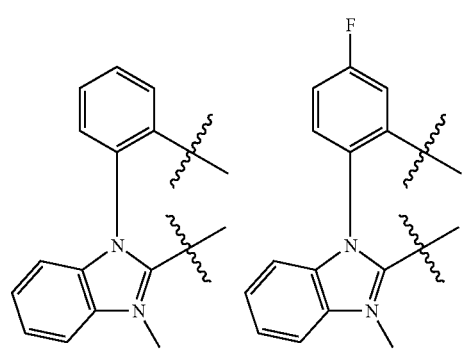
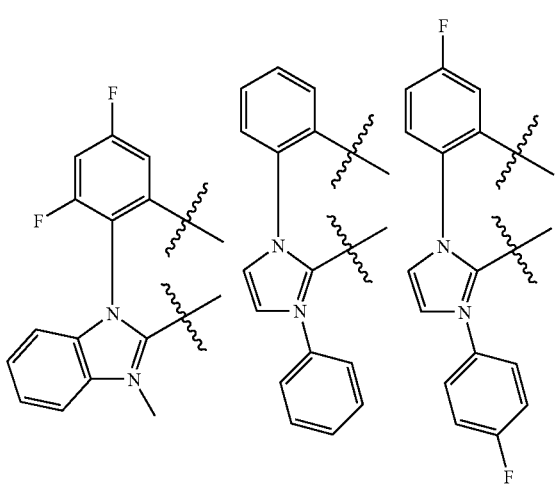
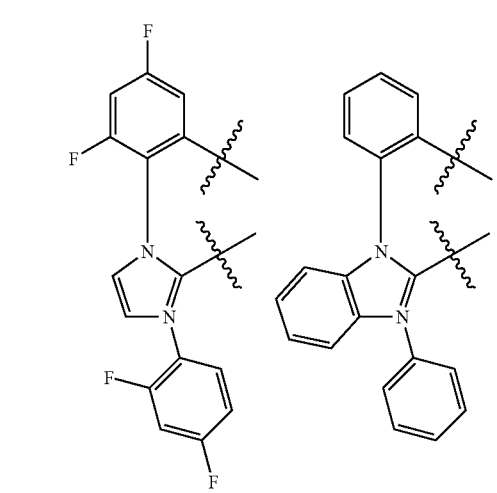
-continued
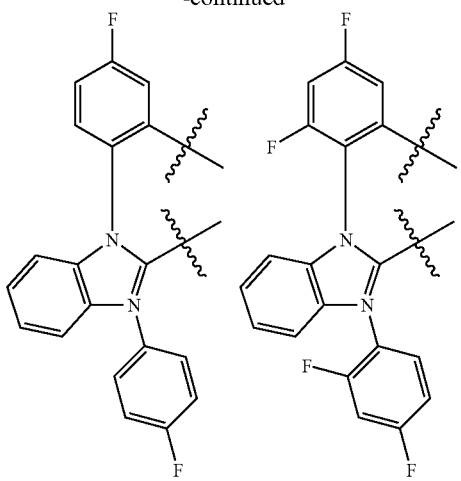
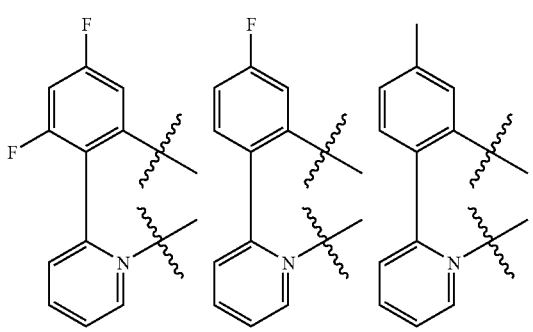
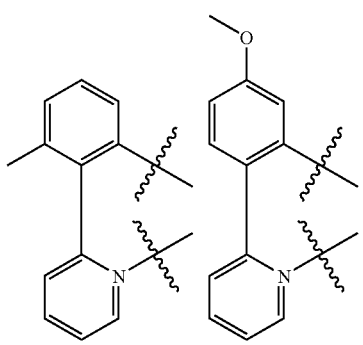
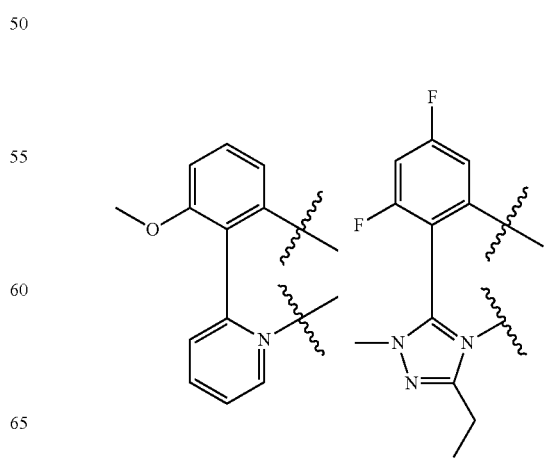

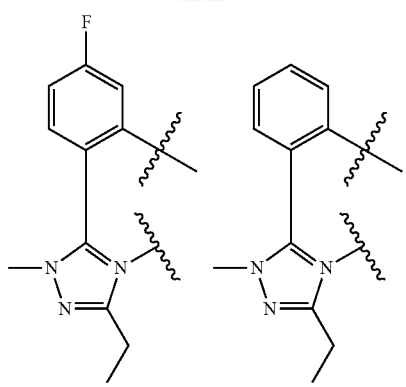
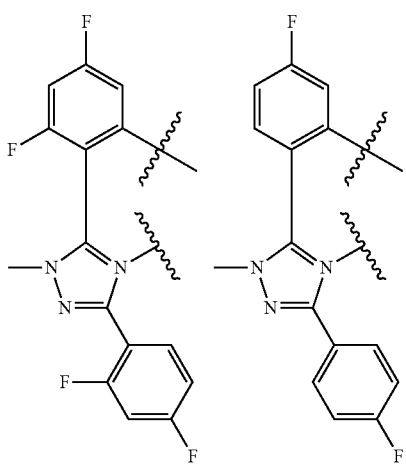
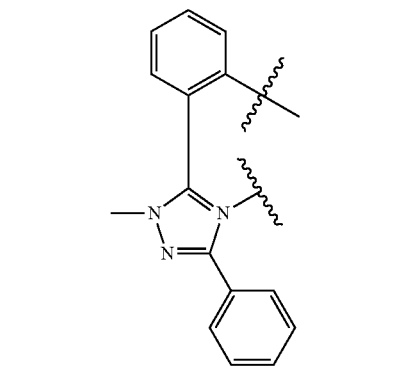
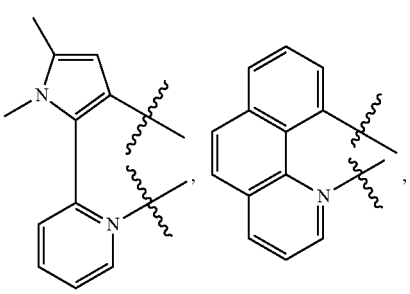
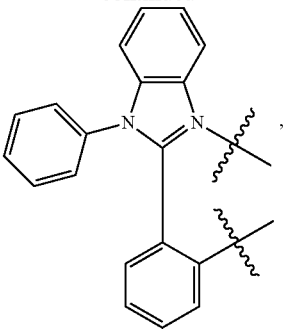
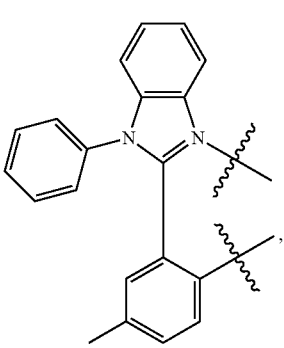
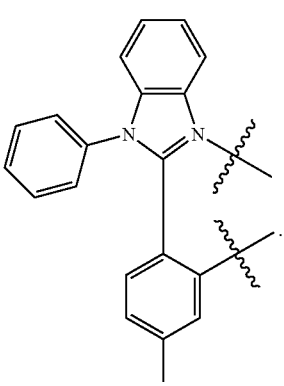
2. The phosphor material according to claim 1, wherein said C1-C22 halo-alkyl group is independently selected from $CF_3$, $C_2F_5$.
3. The phosphor material according to claim 1, wherein the formula of the phosphor material is as following:
4. The phosphor material according to claim 1, wherein the formula of the phosphor material is as following:

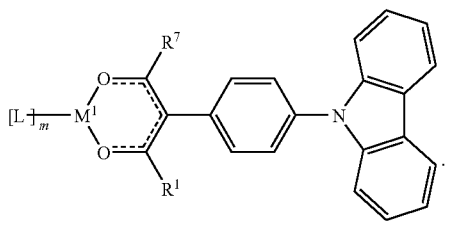

5. The phosphor material according to claim 1, wherein the formula of the phosphor material is as following:

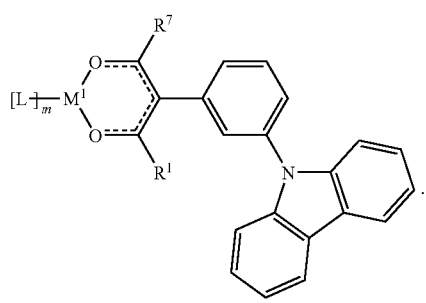

6. The phosphor material according to claim 1, wherein the phosphor material is applied in white light Organic Light Emitting Diodes (WOLEDs) for emitting orange or yellow light, wherein the WOLEDs further comprises a blue emissive layer, wherein the emitting orange or yellow light from the phosphor material can be mixed with the blue emitting light from the blue emissive layer and then produce white light.

7. A phosphor material, the phosphor material comprises a general formula as following:

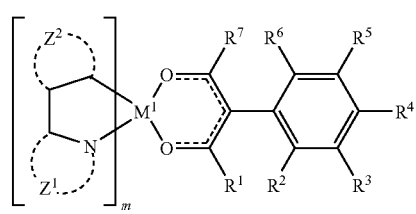

wherein $M^1$ is selected from Pt or Ir, and the value of m is 1 or 2; wherein $R^1$ and $R^7$ can be identical or different, and $R^1$ and $R^7$ can be independently selected from the group consisting of the following: H atom, halogen atom, C1-C22 alkyl group, and C1-C22 halo-alkyl group; wherein $R^2$, $R^3$, $R^4$, $R^5$, and $R^6$ can be identical or different, and $R^2$, $R^3$, $R^4$, $R^5$, and $R^6$ are independently selected from the group consisting of the following: H atom, halogen atom, C1-C22 alkyl group, and C1-C22 halo-alkyl group, C6-C22 aryl group, and 5 to 7 membered heterocyclic group with 1 to 4 heteroatom(s) selected from the group consisting of the following: N, O, B, P, and Si; wherein the C6-C22 aryl group, and 5 to 7 membered heterocyclic group is/are selected from one or the combination of the group consisting of the following:

wherein at least one of $R^3$, $R^4$, and $R^5$ is not H atom; wherein $Z^1$ represents a C3-C15 aromatic heterocyclic group with N atom(s), or a C3-C15 aromatic heterocyclic group with N atom(s) having at least one halo-substituent group(s), wherein $Z^1$ can further comprises a nitrogen-containing single ring to nitrogen-containing fused rings wherein the number of the fused rings is not larger than 5; wherein $Z^2$ represents a single ring or a fused ring comprising not larger than five rings, wherein each ring is selected from the group consisting of: a six membered ring, a five membered ring, a six membered ring with at least one halo-substituent group(s), and a five membered ring with at least one halo-substituent group(s).

8. The phosphor material according to claim 7, wherein the formula of said phosphor material is as following:

9. The phosphor material according to claim 7, wherein the formula of said phosphor material is as following:

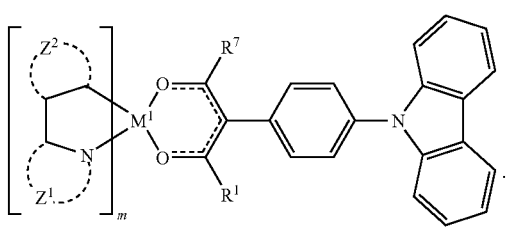

10. The phosphor material according to claim 7, wherein the formula of said phosphor material is as following:

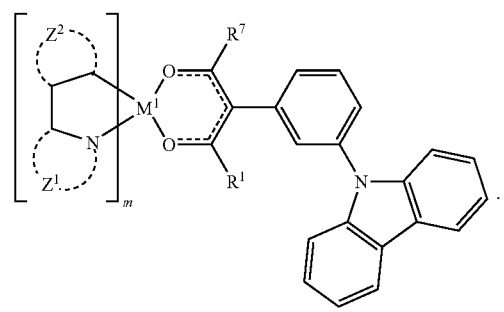

11. The phosphor material according to claim 7, wherein the formula of said phosphor material is selected from one of the group consisting of the following:

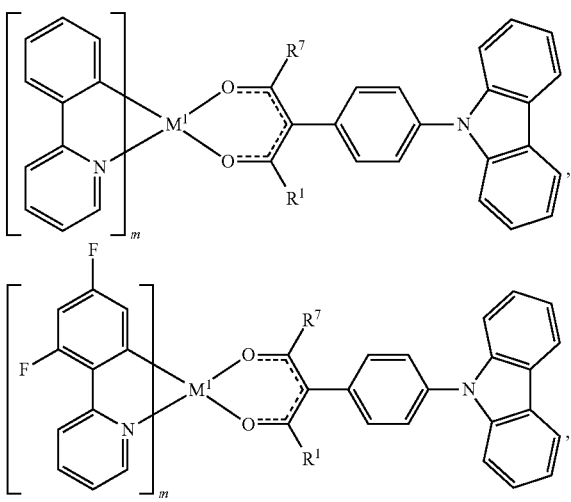

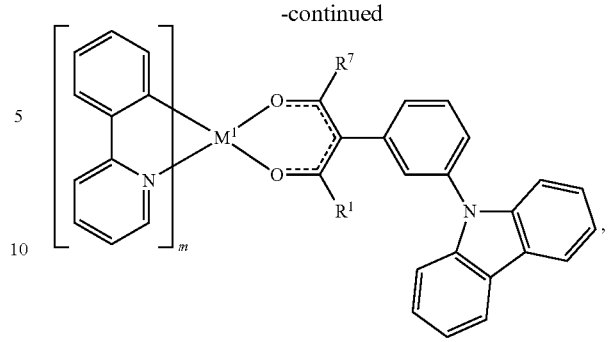

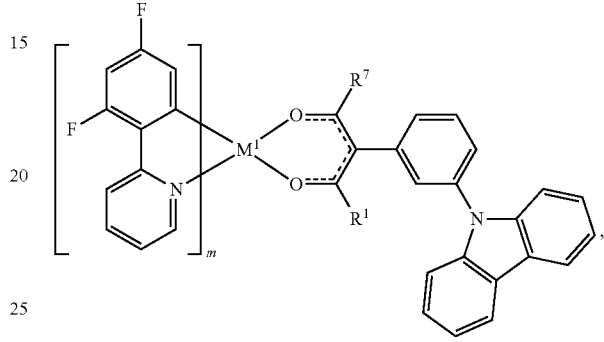

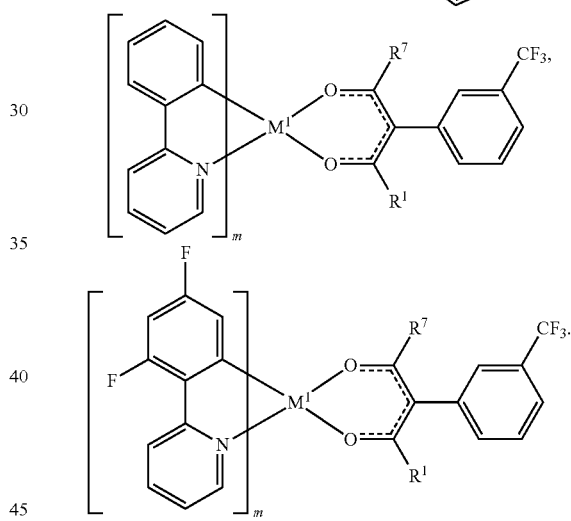

12. The phosphor material according to claim 7, wherein the phosphor material is employed as the major component of a phosphorescent emissive layer.

13. The phosphor material according to claim 7, wherein said phosphor material is employed as non-doped emissive layer in white light Organic Light Emitting Diodes (WOLEDs).

14. The phosphor material according to claim 7, wherein said phosphor material is applied in white light Organic Light Emitting Diodes (WOLEDs) for emitting orange or yellow light, wherein the WOLEDs further comprises a blue emissive layer, wherein the emitting orange or yellow light from the phosphor material can be mixed with the blue emitting light from the blue emissive layer and then produce white light.

15. An OLED comprising one pair of electrodes, and at least one organic layer positioned between the electrodes, wherein the organic layer(s) comprise(s) an emissive layer, wherein at least one layer of the organic layer(s) comprises Pt complex or Ir complex, wherein the mentioned complex comprises an aryl substituted beta-diketone ancillary ligand, wherein the general formula of the Pt (or Ir) complex is as following:

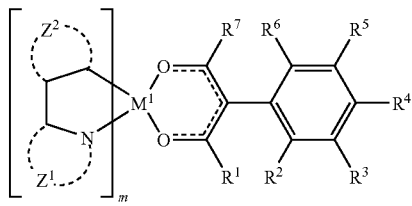

wherein $M^1$ is selected from Pt or Ir, and the value of m is 1 or 2; wherein $R^1$ and $R^7$ can be identical or different, and $R^1$ and $R^7$ can be independently selected from the group consisting of the following: H atom, halogen atom, C1-C22 alkyl group, and C1-C22 halo-alkyl group; wherein $R^2$, $R^3$, $R^4$, $R^5$, and $R^6$ can be identical or different, and $R^2$, $R^3$, $R^4$, $R^5$, and $R^6$ are independently selected from the group consisting of the following: H atom, halogen atom, C1-C22 alkyl group, and C1-C22 halo-alkyl group, C6-C22 aryl group, and 5 to 7 membered heterocyclic group with 1 to 4 heteroatom(s) selected from the group consisting of the following: N, O, B, P, and Si; wherein the C6-C22 aryl group or the heterocyclic group(s) is/are independently selected from one of the group consisting of the following:

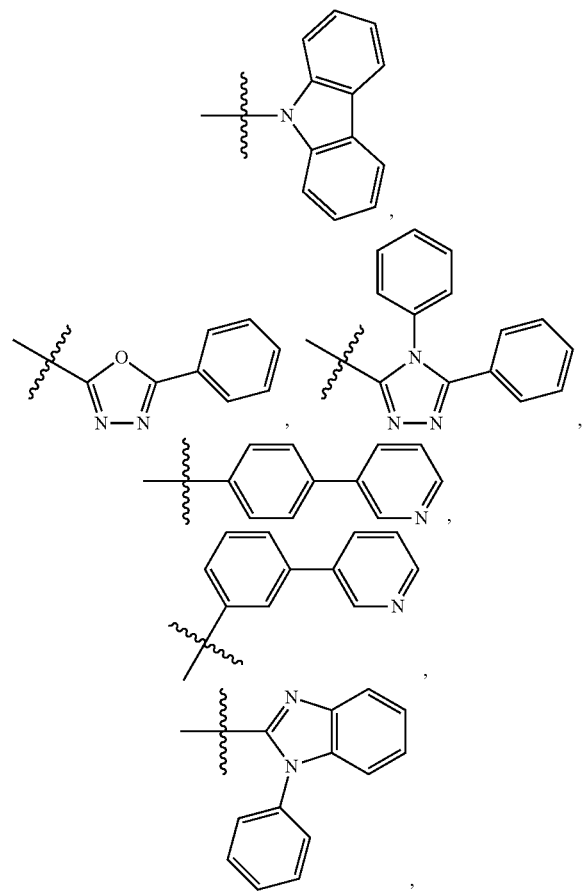

wherein at least one of $R^3$, $R^4$, and $R^5$ is not H atom; wherein $Z^1$ represents C3-C15 aromatic heterocyclic group with N atom(s), or C3-C15 aromatic heterocyclic group with N atom(s) having at least one halo-substituent group(s), wherein $Z^1$ further comprises a nitrogen-containing single ring to nitrogen-containing fused rings wherein the fused ring comprises not larger than five rings; wherein $Z^2$ represents a single ring or a fused ring wherein the fused ring comprises not larger than five rings; wherein each ring is selected from the group consisting of: a six membered ring, a five membered ring, a six membered ring with at least one halo-substituent group(s), and a five membered ring with at least one halo-substituent group(s).

16. The OLED according to claim 15, wherein the formula of the Pt (or Ir) complex is as following:

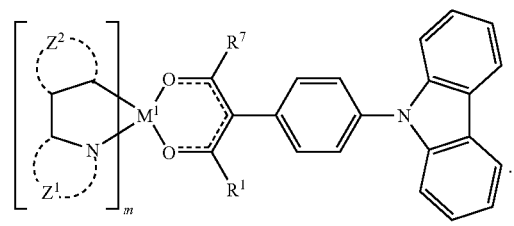

17. The OLED according to claim 15, wherein the formula of the Pt (or Ir) complex is as following:

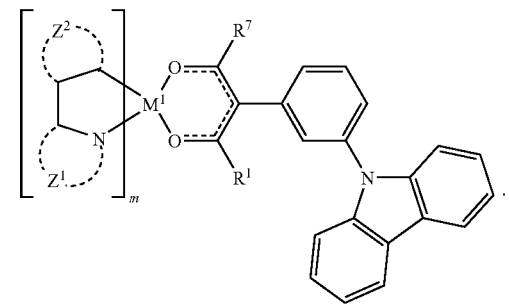

18. The OLED according to claim 15, wherein the formula of the Pt (or Ir) complex is as following:

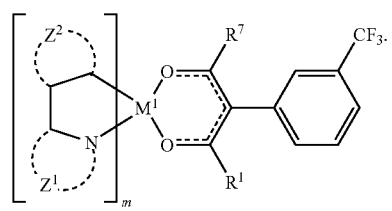
* * * * *